(12) United States Patent
Andersson et al.

(10) Patent No.: US 7,732,137 B2
(45) Date of Patent: Jun. 8, 2010

(54) SELECTING ANIMALS FOR DESIRED GENOTYPIC OR POTENTIAL PHENOTYPIC PROPERTIES

(75) Inventors: Leif Andersson, Uppsala (SE); Goran Andersson, Uppsala (SE); Michel Georges, Villers-aux-Tours (BE); Nadine Buys, Leuven (BE)

(73) Assignees: University of Liege, Liege (BE); Melica HB, Uppsala (SE); Gentec N.V., Lokeren (BE)

( * ) Notice: Subject to any disclaimer, the term of this patent is extended or adjusted under 35 U.S.C. 154(b) by 0 days.

(21) Appl. No.: 11/357,718

(22) Filed: Feb. 17, 2006

(65) Prior Publication Data

US 2007/0006333 A1 Jan. 4, 2007

Related U.S. Application Data

(63) Continuation-in-part of application No. 11/177,498, filed on Jul. 8, 2005, now abandoned, which is a continuation of application No. PCT/EP2004/000149, filed on Jan. 9, 2004.

(30) Foreign Application Priority Data

Jan. 10, 2003 (EP) .................................. 03075091

(51) Int. Cl.
*C12Q 1/68* (2006.01)
(52) U.S. Cl. .......................................... 435/6
(58) Field of Classification Search ........................ None
See application file for complete search history.

(56) References Cited

FOREIGN PATENT DOCUMENTS

| WO | WO 00/36143 | | 6/2000 |
|----|----|----|----|
| WO | WO 00/36143 A2 | * | 6/2000 |
| WO | WO 0036143 A2 | * | 6/2000 |
| WO | WO 2004/063386 | | 7/2004 |

OTHER PUBLICATIONS

Bell et al. ("Isolation of the human insulin-like growth factor genes: insulin-like growth factor II and insulin genes are contiguous" Proc Natl Acad Sci U S A. Oct. 1985;82(19):6450-4).*
Hirooka et al. ("A whole-genome scan for quantitative trait loci affecting teat number in pigs" J Anim Sci. Sep. 2001;79(9):2320-6).*
Lucentini et al (The Scientist (2004) vol. 18).*
Wacholder et al (J. Natl. Cancer Institute (2004) 96(6):434-442).*
Baylin and Bestor (Cancer Cell. May 2002;1(4):299-305).*
Zhu et al. ("Use of DNA methylation for cancer detection and molecular classification" J Biochem Mol Biol. Mar. 31, 2007;40(2)135-41).*
Pandya et al. (American Journal of Human Genetics 1994; 55(3) Suppl:A161).*
Caricasole et al., "Transactivation of mouse insulin-like growth factor II (IGF-II) gene promoters by the AP-1 complex." Nucleic Acids Research. 1993. pp. 1873-1879. vol. 21. No. 8.
Armarger et al., "Comparitive sequence analysis of the INS-IGF2-H19 gene cluster in pigs," Mammalian Genome, 200. pp. 388-398. vol. 13.
Van Laere et al.. "A regulatory mutataion in IGF2 causes a major QTL effect on muscle growth in the pig." Nature. Oct. 23, 2003. pp. 832-836. vol. 425. No. 6960.

* cited by examiner

*Primary Examiner*—Christopher M. Babic
(74) *Attorney, Agent, or Firm*—TraskBritt

(57) ABSTRACT

The invention relates to methods to select animals, such as mammals, particularly domestic animals, such as breeding animals or animals destined for slaughter, for having desired genotypic or potential phenotypic properties, in particular, related to muscle mass and/or fat deposition lean meat, lean back fat, sow prolificacy and/or sow longevity. Provided is a method for selecting an animal for having desired genotypic or potential phenotypic properties comprising testing the animal, a parent of the animal or its progeny for the presence of a nucleic acid modification affecting the activity of an evolutionary conserved CpG island, located in intron 3 of an IGF2 gene and/or for the presence of a nucleic acid modification affecting binding of a nuclear factor to an IGF2 gene.

8 Claims, 9 Drawing Sheets

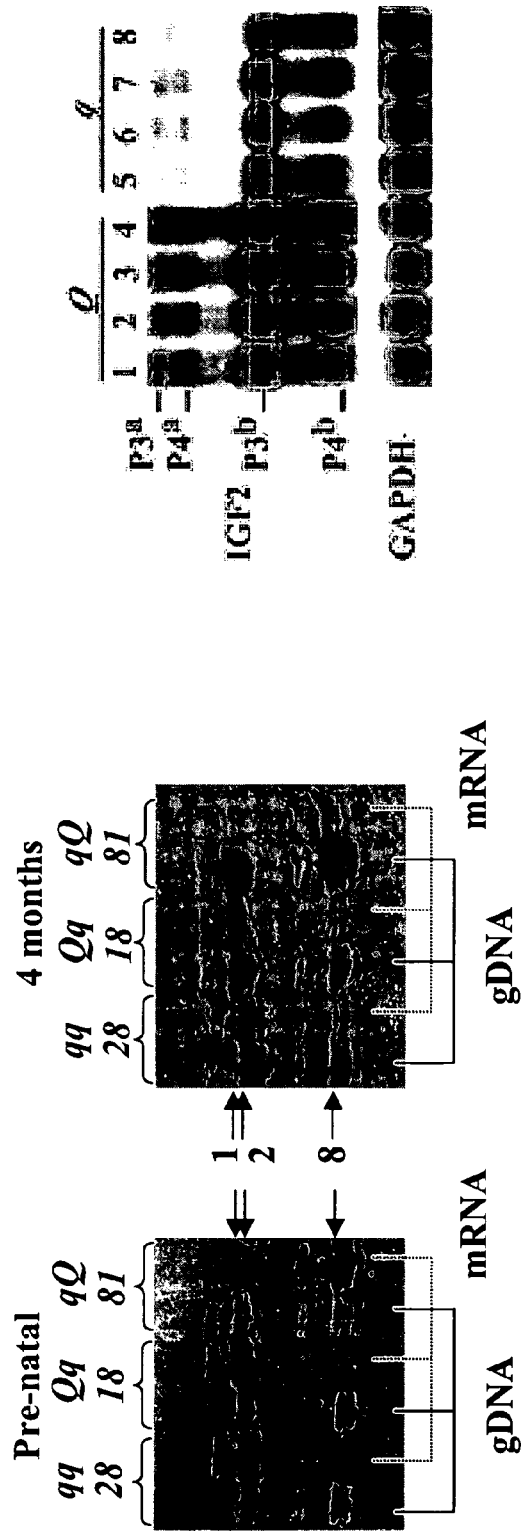
Fig. 6A
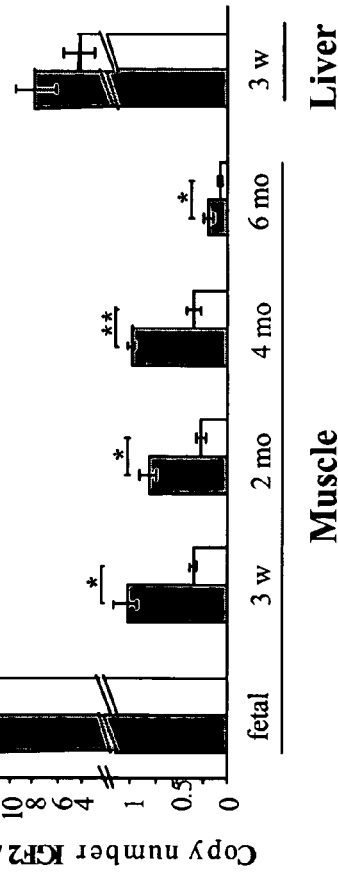
Fig. 6B
Fig. 6C

SELECTING ANIMALS FOR DESIRED GENOTYPIC OR POTENTIAL PHENOTYPIC PROPERTIES

CROSS-REFERENCE TO RELATED APPLICATION

This application is a continuation-in-part of U.S. Ser. No. 11/177,498 filed on Jul. 8, 2005, now abandoned which is a continuation of PCT International Patent Application No. PCT/EP04/000149, filed on Jan. 9, 2004, designating the United States of America, and published, in English, as PCT International Publication No. WO 2004/063386 A2 on Jul. 29, 2004, which application claims priority to European Patent Application Serial No. 03075091.3 filed on Jan. 10, 2003, the contents of the entirety of each are incorporated herein by this reference.

TECHNICAL FIELD

The invention relates to biotechnology generally and, more particularly, to methods of selecting animals, such as mammals, in particular, domestic animals, such as breeding animals or animals destined for slaughter, for having desired genotypic or potential phenotypic properties, in particular, related to muscle mass and/or fat deposition or, in the case of mammals, to teat number.

BACKGROUND

Herein, a domestic animal is defined as an animal being purposely selected, or having been derived from an animal having been purposely selected, for having desired genotypic or potential phenotypic properties.

Domestic animals provide a rich resource of genetic and phenotypic variation; traditionally, domestication involves selecting an animal or its offspring for having desired genotypic or potential phenotypic properties. This selection process has in the past century been facilitated by growing understanding and utilization of the laws of Mendelian inheritance. One of the major problems in breeding programs of domestic animals is the negative genetic correlation between reproductive capacity and production traits. This is, for example, the case in cattle (a high milk production generally results in slim cows and bulls), poultry (broiler lines have a low level of egg production and layers have generally very low muscle growth), pigs (very prolific sows are, in general, fat and have comparatively less meat), or sheep (high prolific breeds have low carcass quality and vice versa). PCT International Patent Application WO 00/36143 provides a method for selecting an animal for having desired genotypic or potential phenotypic properties comprising testing the animal for the presence of a parentally imprinted qualitative or quantitative trait locus (QTL). Knowledge of the parental imprinting character of various traits allows selection of, for example, sire lines homozygous for a paternally imprinted QTL, for example, linked with muscle production or growth; the selection for such traits can thus be less stringent in dam lines in favor of the reproductive quality.

The phenomenon of genetic or parental imprinting has earlier never been utilized in selecting domestic animals; it was never considered feasible to employ this elusive genetic characteristic in practical breeding programs. A breeding program, wherein knowledge of the parental imprinting character of a desired trait, as demonstrated herein is utilized, increases the accuracy of the breeding value estimation and speeds up selection compared to conventional breeding programs. For example, selecting genes characterized by paternal imprinting is provided to help increase uniformity; a (terminal) parent homozygous for the "good or wanted" alleles will pass them to all offspring, regardless of the other parent's alleles, and the offspring will all express the desired parent's alleles. This results in more uniform offspring. Alleles that are interesting or favorable from the maternal side are often the ones that have opposite effects to alleles from the paternal side. For example, in meat animals such as pigs, alleles linked with meat or carcass quality traits such as intramuscular fat or muscle mass could be fixed in the dam lines while alleles linked with reduced back fat could be fixed in the sire lines. Other desirable combinations are, for example, fertility, teat number and/or milk yield in the female line with increased growth rates, reduced back fat and/or increased muscle mass in the male lines.

The purpose of breeding programs in livestock is to enhance the performances of animals by improving their genetic composition. In essence, this improvement accrues by increasing the frequency of the most favorable alleles for the genes influencing the performance characteristics of interest. These genes are referred to as QTL. Until the beginning of the nineties, genetic improvement was achieved via the use of biometrical methods, but without molecular knowledge of the underlying QTL. Now, the identification of causative mutations for Quantitative Trait Loci (QTLs) is a major hurdle in genetic studies of multifactorial traits and disorders. The imprinted IGF2-linked QTL is one of the major porcine QTLs for body composition. It was first identified in intercrosses between the European Wild Boar and Large White domestic pigs and between Piétrain and Large White pigs.[1, 2] The data showed that alleles from the Large White and Piétrain breed, respectively, were associated with increased muscle mass and reduced back-fat thickness, consistent with the existing breed differences in the two crosses. A paternally expressed IGF2-linked QTL was subsequently documented in intercrosses between Chinese Meishan and Large White/Landrace pigs[3] and between Berkshire and Large White pigs.[4] In both cases, the allele for high muscle mass was inherited from the lean Large White/Landrace breed. However, there are a large number of potentially important elements that may influence IGF2 function. Recent sequence analysis (Amarger et al. 2002) provided a partial sequence of the INS-IGF2-H19 region and revealed as many as 97 conserved elements between human and pig.

DISCLOSURE OF THE INVENTION

The invention provides a method for selecting an animal for having desired genotypic or potential phenotypic properties comprising testing the animal for the presence of a qualitative or quantitative trait locus (QTL). Here, we show that a paternally expressed QTL affecting muscle mass, fat deposition and teat number is caused by a single nucleotide substitution in intron 3 of IGF2. The mutation occurs in an evolutionary conserved CpG island that is hypomethylated in skeletal muscle. The function of the conserved CpG island was not known before. IGF2-intron3-nt3072 is part of the evolutionary conserved CpG island with a regulatory function, located between Differentially Methylated Region 1 (DMR1) and a matrix attachment region previously defined in mice.[11-13] The 94 bp sequence around the mutation shows about 85% sequence identity to both human and mouse, and the wild-type nucleotide at IGF2-intron3-nt3072 is conserved among the three species (FIG. 4A).

A qualitative trait nucleotide (QTN) occurs three bp downstream of an eight bp palindrome also conserved between the three species. The methylation status of the 300 bp fragment centered on IGF2-intron3-nt3072 and containing 50 CpG dinucleotides was examined by bisulphite sequencing in four-month-old $Q^{pat}/q^{mat}$ and $q^{pat}/Q^{mat}$ animals. In skeletal muscle, paternal and maternal chromosomes were shown to be essentially unmethylated (including the IGF2-intron3-nt3071 C residue) irrespective of the QTL genotype of the individual (3.4% of CpGs methylated on average; FIG. 5A). The CpG island was more heavily and also differentially methylated in liver, 33% of the CpGs were methylated on the maternal alleles versus 19% on the paternal allele. Unexpectedly, therefore, this CpG island behaves as a previously unidentified DMR in liver, the repressed maternal allele being more heavily methylated than the paternal allele, which is the opposite of what is documented for the adjacent DMR1 in the mouse.

To further uncover a function for this element, we performed electrophoretic mobility shift analyses (EMSA) using 27 bp oligonucleotides spanning the QTN and corresponding to the wild-type (q) and mutant (Q) sequences. Nuclear extracts from murine C2C12 myoblast cells, human HEK293 cells, and human HepG2 cells were incubated with radioactively labeled q or Q oligonucleotides. One specific band shift (complex C1 in FIG. 5B) was obtained with the wild-type (q) but not the mutant (Q) probe using extracts from C2C12 myoblasts; similar results were obtained using both methylated and unmethylated probes. A band shift with approximately the same migration, but weaker, was also detected in extracts from HEK293 and HepG2 cells. The specificity of the complex was confirmed since competition was obtained with ten-fold molar excess of unlabeled q probe, whereas a 50-fold excess of unlabeled Q probe did not achieve competition (FIG. 5B). Thus, the wild-type sequence binds a nuclear factor, and this interaction is abrogated by the mutation. This also means that there could be other mutations in this region that are important in pigs or other species.

Furthermore, our data show that the CpG island contains both Enhancer and Silencer functions so that there may be several nuclear factors binding to this CpG island except for the one already shown here. Our results provide a method for isolating such nuclear factors. We provide a stretch of oligonucleotides that can be used to fish out such proteins. Pigs carrying the mutation have a three-fold increase in IGF2 mRNA expression in postnatal muscle. The mutation abrogates in vitro interaction with a nuclear factor, most likely a repressor. The mutation has experienced a selective sweep in several pig breeds.

As further described in the Detailed Description herein, we have used a haplotype-sharing approach to refine the map position of the QTL.[5] We assumed that a new allele (Q) promoting muscle development occurred g generations ago on a chromosome carrying the wild-type allele (q). We also assumed that the favorable allele has gone through a selective sweep due to the strong selection for lean growth in commercial pig populations. Twenty-eight chromosomes with known QTL status were identified by marker-assisted segregation analysis using cross-bred Piétrain and Large White boars. All 19 Q-bearing chromosomes shared a haplotype in the 90 kilobase pairs (kb) interval between the microsatellites PULGE1 and SW2C9 (IGF2 3'-UTR), which was not present among the q chromosomes and was, therefore, predicted to contain the QTL. In contrast, the nine q chromosomes exhibited six distinct marker haplotypes in the same interval. This region is part of the CDKN1C-HR19 imprinted domain and contains INS and IGF2 as the only known paternally expressed genes. With this insight, the invention provides a method for selecting an animal for having desired genotypic or potential phenotypic properties comprising testing the animal, a parent of the animal or its progeny for the presence of a nucleic acid modification affecting the activity of an evolutionary conserved CpG island, located in intron 3 of an IGF2 gene and/or affecting binding of a nuclear factor to an IGF2 gene.

In a preferred embodiment, the invention provides a method for selecting an animal for having desired genotypic or potential phenotypic properties comprising testing a nucleic acid sample from the animal for the presence of the single nucleotide substitution. A nucleic acid sample can be obtained, in general, from various parts of the animal's body by methods known in the art. Traditional samples for the purpose of nucleic acid testing are blood samples or skin or mucosal surface samples, but samples from other tissues can be used as well, in particular, sperm samples, oocyte or embryo samples can also be used. In such a sample, the presence and/or sequence of a specific nucleic acid, be it DNA or RNA, can be determined with methods known in the art, such as hybridization or nucleic acid amplification or sequencing techniques known in the art. The invention also provides testing such a sample for the presence of nucleic acid wherein the QTN or allele associated therewith is associated with the phenomenon of parental imprinting, for example, where it is determined whether a paternal or maternal allele comprising the QTN is capable of being predominantly expressed in the animal.

In a preferred embodiment, the invention provides a method wherein the nuclear factor is capable of binding to a stretch of nucleotides, which in the wild-type pig, mouse or human IGF2 gene, is part of an evolutionary conserved CpG island, located in intron 3 of the IGF2 gene. Binding should preferably be located at a stretch of nucleotides spanning a QTN (qualitative trait nucleotide), which comprises a nucleotide (preferably a G to A) transition, which in the pig is located at IGF2-intron3-nt3072. It is preferred that the stretch is functionally equivalent to the sequence as shown in FIG. 4, which comprises the sequence 5'-GATCCTTCGCCTAG-GCTC(A/G)CAGCGCGGGAGCGA-3' (SEQ ID NO: 1) identifying the overlap with the QTN, wherein functional equivalence preferably entails that the stretch is spanning the QTN, and preferably overlaps with at least two or three nucleotides at or on both sides of the QTN, although the overlaps may be longer. Also, functional equivalence entails a sequence homology of at least 50%, preferably at least 60%, more preferably at least 70%, even more preferably at least 80%, most preferred at least 90%, of the stretch overlapping the QTN. The stretch is preferably from at least five to at about 94 nucleotides long, more preferably from about ten to 50, most preferably from about 15 to 35 nucleotides, and it is preferred that it comprises a palindromic octamer sequence as identified in FIG. 4. In a preferred embodiment, the invention provides a method wherein the nucleic acid modification comprises a nucleotide substitution, wherein the pig the substitution comprises a G to A transition at IGF2-intron3-nt3072. Abrogating or reducing binding of the nuclear factor to the IGF2 gene allows for modulating IGF2 mRNA transcription in a cell provided (naturally or by recombinant means) with the gene.

To further characterize the functional significance of the IGF2 Q mutation, we studied its effect on transcription by employing a transient transfection assay in mouse C2C12 myoblasts. We made Q and q constructs containing a 578 bp fragment from the actual region inserted in front of a Luciferase reporter gene driven by the herpes thymidine kinase (TK) minimal promoter. The two constructs differed only by the IGF2-intron3-nt3072G→A transition. The ability of the IGF2 fragments to activate transcription from the heterologous promoter was compared with the activity of the TK-promoter alone. The presence of the q-construct caused a two-fold increase of transcription, whereas the Q-construct caused a significantly higher, seven-fold, increase (FIG. 5C). Our interpretation of this result, in light of the results from the EMSA experiment, is that the Q mutation abrogates the interaction with a repressor protein that modulates the activity of a putative IGF2 enhancer present in this CpG island. This view is consistent with our in silico identification of potential binding sites for both activators and repressors in this intronic DNA fragment.[14]

The in vivo effect of the mutation on IGF2 expression was studied in a purpose-built Q/q×Q/q intercross counting 73 offspring. As a deletion encompassing DMR0, DMR1, and the associated CpG island derepresses the maternal IGF2 allele in mesodermal tissues in the mouse,[12] we tested the effect of the intron3-nt3072 mutation on IGF2 imprinting in the pig. This was achieved by monitoring transcription from the paternal and maternal IGF2 alleles in tissues of q/q, $Q^{pat}/q^{mat}$, and $q^{pat}/Q^{mat}$ animals that were heterozygous for the SWC9 microsatellite located in the IGF2 3'UTR. Imprinting could not be studied in Q/Q animals which were all homozygous for SWC9. Before birth, IGF2 was shown to be expressed exclusively from the paternal allele in skeletal muscle and kidney, irrespective of the QTL genotype of the fetuses. At four months of age, weak expression from the maternal allele was observed in skeletal muscle, however, at comparable rates for all three QTL genotypes (FIG. 6, Panel A). Only the paternal allele could be detected in four month old kidney (data not shown). Consequently, the mutation does not seem to affect the imprinting status of IGF2. The partial derepression of the maternal allele in skeletal muscle of all QTL genotypes may, however, explain why in a previous study muscular development was found to be slightly superior in $q^{pat}/Q^{mat}$ versus q/q animals, and in Q/Q versus $Q^{pat}/q^{mat}$ animals.[2]

The Q allele was expected to be associated with an increased IGF2 expression since IGF2 stimulates myogenesis.[6] To test this, we monitored the relative mRNA expression of IGF2 at different ages in the Q/q×Q/q intercross using both Northern blot analysis and real-time PCR (FIG. 6, Panels B and C). The expression levels in fetal muscle and postnatal liver was about ten-fold higher than in postnatal muscle. No significant difference was observed in fetal samples or in postnatal liver samples, but a significant three-fold increase of postnatal IGF2 mRNA expression in skeletal muscle was observed in (Q/Q or $Q^{pat}/q^{mat}$) versus ($q^{pat}/Q^{mat}$ or q/q) progeny. Herewith, the invention provides a method for modulating mRNA transcription of an IGF2 gene in a cell or organism provided with the gene comprising modulating binding of a nuclear factor to an IGF2 gene, in particular, wherein the nuclear factor is capable of binding to a stretch of nucleotides (as identified above), which in the wild-type pig, mouse or human IGF2 gene, is part of an evolutionary conserved CpG island, located in intron 3 of the IGF2 gene. The significant difference in IGF2 expression revealed by real-time PCR was confirmed using two different internal controls, GAPDH (FIG. 6, Panel C) and HPRT.[15] We found an increase of all detected transcripts originating from the three promoters (P2-P4) located downstream of the mutated site. Combined, these results provide strong evidence for IGF2 being the causative gene. The lack of significant differences in IGF2 mRNA expression in fetal muscle and postnatal liver are consistent with our previous QTL study showing no effect of the IGF2 locus on birth weight and weight of liver.[2]

Accordingly, a method according to the invention is herein provided allowing testing for and modulation of desired genotypic or potential phenotypic properties comprising muscle mass, fat deposition or teat numbers (of mammals). Such testing is applicable in man and animals alike (animals herein defined as including humans). In humans, it is, for example, worthwhile to test for the presence of a nucleic acid modification affecting the activity of an evolutionary conserved CpG island, located in intron 3 of an IGF2 gene or affecting binding of a nuclear factor to an IGF2 gene, as provided herein, to test, for example, the propensity or genetic predisposition or likelihood of muscle growth or muscularity in humans versus propensity or genetic predisposition or the likelihood of obesity. In domestic animals, such testing may be undertaken to select the best or most suitable animals for breeding, or to preselect domestic animals destined for slaughter. An additional trait to be selected for concerns teat number, a quality highly valued in sow lines to allow for suckling large litters. A desirable breeding combination as provided herein comprises, for example, increased teat number in the female line with increased growth rates, and reduced back fat and/or increased muscle mass in the male lines. It is herein also shown that the mutation influences teat number. The Q allele that is favorable with respect to muscle mass and reduced back fat is the unfavorable allele for teat number. This strengthens the possibility of using the paternal imprinting character of this QTL in breeding programs. Selecting maternal lines for the q allele will enhance teat number, a characteristic that is favorable for the maternal side. On the other hand, paternal lines can be selected for the Q allele that will increase muscle mass and reduce back fat, characteristics that are of more importance in the paternal lines. Terminal sires that are homozygous QQ will pass the full effect of increased muscle mass and reduced back fat to the slaughter pigs, while selection of parental sows that express the q allele will allow for the selection of sows that have more teats and suckle more piglets without affecting slaughter quality.

As indicated above, the insulin-like growth factor 2 (IGF2) gene was mapped to the distal tip of the short arm on chromosome 2 in swine. Gene mapping studies indicated that this paternally expressed QTL at the IGF2 gene region has a large effect on back fat thickness and carcass leanness (e.g., Jeon et al. (1999), *Nature Genetics* 21, 157-158; Nezer et al. (1999), *Nature Genetics* 21, 155-156). Recently, a mutation in the regulatory region of the IGF2 gene has been identified to be the cause underlying the QTL effect on muscle growth and fat deposition (Van Laere et al. (2003), *Nature* 425:832-836). This single nucleotide substitution (G-A), located at position 3072 in the intron 3 of IGF2 gene, increases gene expression of IGF2 in muscle three-fold, stimulates muscle growth at the expense of back fat and results in leaner swine carcass and lower back fat.

The large effect of the QTL on lean meat and back fat without influence on growth or meat quality, makes this an attractive QTL to use in the breeding program. Terminal sires have been selected to be homozygous for the lean allele (AA) in order to pass the full effect to their offspring. Field results have been reported by several authors (Scheller et al. (2002), *Proceedings of the 27th Annual National Swine Improvement Federation, Des Moines, Iowa, USA*; N. Buys (2003), *Proceedings of the 28th Annual National Swine Improvement Federation, Des Moines, Iowa, USA*, pp 146-149).

It is generally believed that prolificacy and sow longevity is reduced as a result of the genetic selection for increased leanness and lowering fat deposition (see, e.g., P. Mathur and Y. Liu (2003), *Proceedings of the 28th Annual National Swine*

*Improvement Federation, Des Moines, Iowa, USA*, pp 155-163). Body fat deposition is necessary to sustain sow reproduction performance, for example, to support adequate milk production and to limit body weight loss. The selection for leaner carcasses, demanded by the packing industry and consumers, may conflict with the prolificacy and longevity of the sow and lead to increased replacement costs of sows in pig production. The QTN (quantitative trait nucleotide) in the IGF2 gene might provide a possibility to overcome this conflict. The imprinting character of the gene might be used to produce lean slaughter pigs from fatter dams that inherited the wild-type allele from their father (genotype of Grand parent boar=GG), crossed with terminal sires being homozygous for the lean allele (AA). The objective of this experiment was to investigate a possible effect of the QTN at the IGF2 gene on prolificacy and longevity.

The details of the experiment are described in Example 5. It was found that sows that inherited the wild-type allele from their father had significantly more piglets born alive, total born and weaned, while there was no effect on stillborn piglets (see, Example 5, Table 4). No effect on any of these prolificacy data could be observed when data were analyzed according to the allele inherited from the mother (maternal allele). Also, if sows from heterozygous dams were taken into account and grouped according to the maternal allele, again no significant effect on prolificacy could be observed, which was expected since the maternal allele is not expressed.

The parity or average number of cycles per sow was also found to be higher in sows that inherited G from their father as compared to those that received the A allele, which points to a beneficial effect on longevity. This is related to higher litter size since that is a major criterion for elimination in the selection program.

Thus, the IGF2-intron3 G3072A mutation (herein also referred to as "IGF2+" or "A"-allele; the wild-type being the igf2- or G-allele) has an influence on prolificacy and longevity in sows, which allows for the possibility of using the same imprinted QTN for different selection in sire and dam lines. Terminal sires should be homozygous for the lean allele to give uniform and lean slaughter pigs, while dam lines can benefit from a selection for the wild-type allele since this has a beneficial effect on prolificacy and longevity. Because of the imprinted character of the gene, selection for the fatter allele in sow lines will not influence the carcass quality of the offspring.

Thus, the invention provides a method for selecting a domestic animal for having desired genotypic properties comprising testing the animal for the presence of a parentally imprinted quantitative trait locus (QTL) or a mutation therein and to the use of an isolated and/or recombinant nucleic acid comprising a parentally imprinted quantitative trait locus (QTL) or a mutation therein or functional fragment derived thereof to select a breeding animal or animal destined for slaughter for having desired genotypic or potential phenotypic properties. The test may, for instance, comprise testing a sample from the pig for the presence of a quantitative trait locus (QTL) located at a Sus scrofa chromosome 2 mapping at position 2 p1.7., wherein the QTL is paternally expressed, i.e., is expressed from the paternal allele.

In particular, the genotypic or potential phenotypic properties are selected from the group consisting of muscle mass, fat deposition, lean meat, lean back fat, sow prolificacy and sow longevity. In particular, improved sow prolificacy may include such phenotypic expressions as higher teat number, more piglets born alive, higher litter size, higher number of total born and weaned piglets with no effect on stillborn piglets. Improved sow longevity may, in particular, include such phenotypic expressions as parity or average number of cycles per sow.

Thus, the above-described IGF2 mutation influencing lean meat also influences a number of other positive traits and allows for marker-assisted selection in opposite directions in sire and dam lines due to the parentally imprinting character of the mutation. The mutation increases muscle mass at the expense of back fat with, on average, 2% to 4% more lean meat. This effect on leanness is of the same magnitude as reported for the Halothane gene but without any of the well-known deleterious effects on meat quality and animal health. Homozygous-positive terminal sires (IGF2+/IGF2+) will pass the full effect to the slaughter pigs, regardless of the genotype of the mother. Furthermore, such selection principles allow for the possibility to push a far higher proportion of lower grading pigs into the higher payment categories. The experiment described in Example 4 shows that parent sows benefit from inheriting the negative gene (igf2-) from their father: they are more prolific and have an increased longevity. Parent sows are fatter but this will have no effect on the carcass quality of the slaughter pig (see, FIG. 7).

The invention also provides a method for identifying a compound capable of modulating mRNA transcription of an IGF2 gene in a cell or organism provided with the gene comprising providing a first cell or organism having a nucleic acid modification affecting the activity of an evolutionary conserved CpG island, located in intron 3 of an IGF2 gene and/or affecting binding of a nuclear factor to an IGF2 gene and a second cell or organism not having the modification further comprising providing the first or the second cell or organism with a test compound and determining IGF2 mRNA transcription in the first and second cell or organism and selecting a compound capable of modulating IGF2 mRNA transcription. An example of such a compound as identifiable herewith comprises a stretch of oligonucleotides spanning a QTN (qualitative trait nucleotide), which comprises a nucleotide (preferably a G to A) transition, which in the pig is located at IGF2-intron3-nt3072. It is preferred that the stretch is functionally equivalent to the sequence as shown in FIG. 4, which comprises the sequence 5'-GATCCTTCGCCTAG-GCTC(A/G)CAGCGCGGGAGCGA-3' (SEQ ID NO: 1) identifying the overlap with the QTN, wherein functional equivalence preferably entails that the stretch is spanning the QTN, and preferably overlaps with at least two or three nucleotides at or on both sides of the QTN, although the overlaps may be longer. Also, functional equivalence entails a sequence homology of at least 50%, preferably at least 60%, more preferably at least 70%, even more preferably at least 80%, most preferred at least 90% of the stretch overlapping the QTN. The stretch is preferably from at least five to about 94 nucleotides long, more preferably from about ten to 50, most preferably from about 15 to 35 nucleotides, and it is preferred that it comprises a palindromic octamer sequence as identified in FIG. 4.

An alternative compound as provided herein comprises a functional analogue of the stretch, the alternative compound or oligonucleotide analogue functionally at least capable of modulating the activity of an evolutionary conserved CpG island, located in intron 3 of an IGF2 gene and/or modulating binding of a nuclear factor to an IGF2 gene, preferably effecting the modulation at the site of the QTN. In electrophoretic mobility shift analyses (EMSA), such compounds, e.g., in FIG. 2 identified as nuclear factor, or compounds competing with the binding of the factor to the IGF2 gene, can be further identified and selected. A typical example of such an EMSA is given in the detailed description. It is preferred that the nuclear factor is capable of binding to a stretch of nucleotides, which in the wild-type pig, mouse or human IGF2 gene, is part of an evolutionary conserved CpG island, located in intron 3 of the IGF2 gene. Oligonucleotide compounds or probes spanning the QTN are herein provided that have the desired effect. Such compounds or probes are preferably functionally equivalent to the sequence 5'-GATCCTTCGC-CTAGGCTC(A/G)CAGCGCGGGAGCGA-3' (SEQ ID NO: 1).

The invention also provides a method for identifying a compound capable of affecting the activity of an evolutionary conserved CpG island, located in intron 3 of an IGF2 gene and/or modulating binding of a nuclear factor to an IGF2 gene comprising providing a stretch of nucleotides, which in the wild-type pig, mouse or human IGF2 gene, is part of an evolutionary conserved CpG island, located in intron 3 of the IGF2 gene. Such testing may be done with single oligonucleotides or analogues thereof, or with a multitude of such oligonucleotides or analogues in an array fashion, and may further comprise providing a mixture of DNA-binding proteins derived from a nuclear extract of a cell and testing these with the array or analogue or oligonucleotide under study. Testing may be done as well with test compounds provided either singularly or in an array fashion and optionally further comprises providing a test compound and determining competition of binding of the mixture of DNA-binding proteins to the stretch of nucleotides in the presence or absence of the test compound(s). To find active compounds for further study or, eventually, for pharmaceutical use, it suffices to select a compound capable of inhibiting binding of the mixture to the stretch, wherein the stretch is functionally equivalent to the sequence 5'-GATCCTTCGCCTAGGCTC(A/G) CAGCGCGGGAGCGA-3' (SEQ ID NO: 1).

The invention thus provides a compound identifiable with a method as described herein. Such a compound is, for example, derived from a stretch of oligonucleotides spanning a QTN (qualitative trait nucleotide), which comprises a nucleotide (preferably a G to A) transition, which in the pig is located at IGF2-intron3-nt3072. It is preferred that the stretch is functionally equivalent to the sequence as shown in FIG. 4, which comprises the sequence 5'-GATCCTTCGCCTAG-GCTC(A/G)CAGCGCGGGAGCGA-3' (SEQ ID NO:1) identifying the overlap with the QTN, wherein functional equivalence preferably entails that the stretch is spanning the QTN, and preferably overlaps with at least two or three nucleotides at or on both sides of the QTN, although the overlaps may be longer. Also, functional equivalence entails a sequence homology of at least 50%, preferably at least 60%, more preferably at least 70%, even more preferably at least 80%, most preferred at least 90% of the stretch overlapping the QTN. The oligonucleotide compound is preferably from at least five to about 94 nucleotides long, more preferably from about ten to 50, most preferably from about ten to 35 nucleotides, and it is preferred that it comprises a palindromic octamer sequence as identified in FIG. 4.

An alternative compound or functional analogue as provided herein comprises a functional analogue of the oligonucleotide compound, the alternative compound or oligonucleotide analogue functionally at least capable of modulating the activity of an evolutionary conserved CpG island, located in intron 3 of an IGF2 gene and/or modulating binding of a nuclear factor to an IGF2 gene, preferably effecting the modulation at the site of the QTN. For example, in electrophoretic mobility shift analyses (EMSA), such compounds, e.g., in FIG. 2 identified as nuclear factor, or compounds competing with the binding of the factor to the IGF2 gene, can be further identified and selected. A typical example of such an EMSA is given in the detailed description. The invention also provides a pharmaceutical composition comprising a compound as provided herein, and use of such a compound for the production of a pharmaceutical composition for the treatment of obesity, or for the treatment of muscle deficiencies. Furthermore, the invention provides a method for modulating mRNA transcription of an IGF2 gene in a cell or organism provided with the gene comprising treating or providing the cell or organism with a compound as provided herein.

There has been a strong selection for lean growth (high muscle mass and low fat content) in commercial pig populations in Europe and North America during the last 50 years. Therefore, we investigated how this selection pressure has affected the allele frequency distribution of the IGF2 QTL. The causative mutation was absent in a small sample of European and Asian Wild Boars and in several breeds that have not been strongly selected for lean growth (Table 1). In contrast, the causative mutation was found at high frequencies in breeds that have been subjected to strong selection for lean growth. The only exceptions were the experimental Large White population at the Roslin Institute that was founded from commercial breeding stocks in the UK around 1980,[16] as well as the experimental Large White populations used for the Piétrain/Large White intercross;[1] these two populations thus reflect the status in some commercial populations about 20 years ago and it is possible that the IGF2*Q allele is even more predominant in contemporary populations. The results demonstrate that IGF2*Q has experienced a selective sweep in several major commercial pig populations and it has apparently been spread between breeds by cross-breeding.

The results have important practical implications. The IGF2*Q mutation increases the amount of meat produced, at the expense of fat, by 3 to 4 kg for an animal slaughtered at the usual weight of about 100 kg. The high frequency of IGF2*Q among major pig breeds implies that this mutation affects the productivity of many millions of pigs in the Western world. The development of a simple diagnostic DNA test now facilitates the introgression of this mutation to additional breeds. This could be an attractive way to improve productivity in local breeds as a measure to maintain biological diversity. The diagnostic test will also make it possible to investigate if the IGF2*Q mutation is associated with any unfavorable effects on meat quality or any other trait. We and others have previously demonstrated that European and Asian pigs were domesticated from different subspecies of the Wild Boar, and that Asian germplasm has been introgressed into European pig breeds.[17] The IGF2*Q mutation apparently occurred on an Asian chromosome as it showed a very close relationship to the haplotype carried by Chinese Meishan pigs. This explains the large genetic distance that we observed between Q- and q-haplotypes (FIG. 4). However, it is an open question whether the Q mutation occurred before or after the Asian chromosome was introduced into European pigs.

This study provides new insights in IGF2 biology. The role of IGF2 on prenatal development is well documented.[18, 19] Our observation that the Q mutation does not up-regulate IGF2 expression in fetal tissue until after birth, which demonstrates that IGF2 has an important role for regulating postnatal myogenesis. The finding that the sequence around the mutation does not match any known DNA-binding site shows that this sequence binds an earlier unknown nuclear factor.[14] Our results also imply that pharmacological intervention of the interaction between this DNA segment and the corresponding nuclear factor opens up new strategies for promoting muscle growth in humans, such as patients with muscle deficiencies, or for stimulating muscle development at the cost of adipose tissue in obese patients.

Applications of these insights are manifold. Applications in animals typically include diagnostic tests of the specific causative mutation in the pig and diagnostic tests of these and possible other mutations in this CpG island in humans, pigs or other meat producing animals.

It is now also possible to provide for transgenic animals with modified constitution of this CpG island or with modified expression of nuclear factors interacting with this sequence, and the invention provides the use of pharmaceutical compounds (including oligonucleotides) or vaccination to modulate IGF2 expression by interfering with the interaction between nuclear factors and the CpG island provided herein. Thus, instead of selecting animals, one may treat the animals with a drug, if not for producing meat then at least in experimental animals for studying the therapeutic effects of the compounds.

In humans, diagnostic tests of mutations predisposing to diabetes, obesity or muscle deficiency are particularly provided and pharmaceutical intervention to treat diabetes, obesity or muscle deficiency by modulating IGF2 expression based on interfering with the interaction between nuclear factors and the CpG island as provided herein is typically achievable with compounds, such as the above-identified nucleotide stretches or functional analogues thereof as provided herein.

BRIEF DESCRIPTION OF THE FIGURES

FIG. 6: Analysis of IGF2 mRNA expression. (Panel A) Imprinting analysis of IGF2 in skeletal muscle of qq, $Q^{Pat}/q^{Mat}$, and $q^{Pat}/Q^{Mat}$ animals before birth and at four months of age. The QTL and SWC9 genotypes of the analyzed animals are given. In these, the first allele is paternal, the second maternal. The lanes corresponding to PCR product obtained from genomic DNA are marked by continuous lines, those corresponding to RT-PCR products by the dotted lines. The three SWC9 alleles segregating in the pedigree (1, 2, and 8) are marked by arrows. The RT-PCR controls without reverse transcriptase were negative (not shown). (Panel B) Northern blot analysis of skeletal muscle poly(A)$^+$ RNA from three-week-old piglets using IGF2 and GAPDH probes. Animals 1-4 and 5-8 carried a paternal IGF2*Q or *q allele, respectively. P3 and P4 indicate the IGF2 promoter usage and the superscripts a and b indicate the alternative polyadenylation signal used. All four IGF2 transcripts showed a significantly higher relative expression (standardized using GAPDH expression) in the *Q group (P<0.05, Kruskal-Wallis rank sum test, two sided). (Panel C) Results of real-time PCR analysis of IGF2 mRNA expression in skeletal muscle and liver at different developmental phases of pigs carrying paternal IGF2*Q (gray staples) or *q (white staples) alleles. The expression levels were normalized using GAPDH as internal control. Means±SE are given, n=3-11. *=P<0.05, **=P<0.01, Kruskal-Wallis rank sum test, two sided. No significant differences in IGF2 expression levels between genotypes were found in fetal (80 days of gestation) or liver tissues (three weeks). w, week; mo, month.

DETAILED DESCRIPTION OF THE INVENTION

Figure 1:
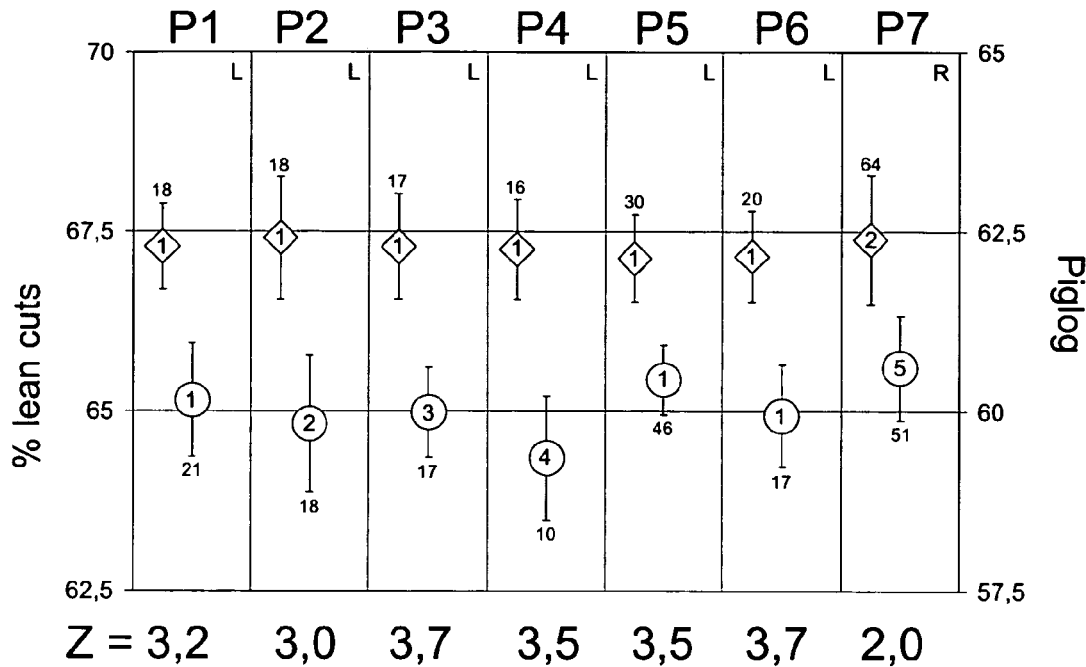
FIG. 1: QTL genotyping by marker-assisted segregation analysis. The graphs show, for 14 paternal half-sib pedigrees (P1, P2, . . . P14), the phenotypic mean±2 standard errors of the offspring sorted in two groups according to the homologue inherited from the sire. The number of offspring in each group is given above and below the error bars, respectively. The upper graph corresponds to the boars that were shown to be heterozygous "Qq" for the QTL, the lower graph to the boars that were shown to be homozygous at the QTL. Pedigrees for which the % lean meat was measured as "% lean cuts" (Nezer et al. 2002) are marked by L(eft axis), those for which "Piglog" was used (see, M&M) are marked by R(ight axis). The graph reports a Z-score for each pedigree, i.e., the log 10 of the $H_1/H_0$ likelihood ratio where $H_1$ assumes that the boar is heterozygous "Qq" for the QTL, while $H_0$ assumes that the boar is homozygous "QQ" or "qq." "Q" alleles associated with a positive allele substitution effect on % lean meat are marked by a diamond, "q" alleles by a circle. The number within the symbols differentiate the "Q" and "q" alleles according to the associated marker haplotype (see results of Example 1 and FIG. 2).
Figure 1:
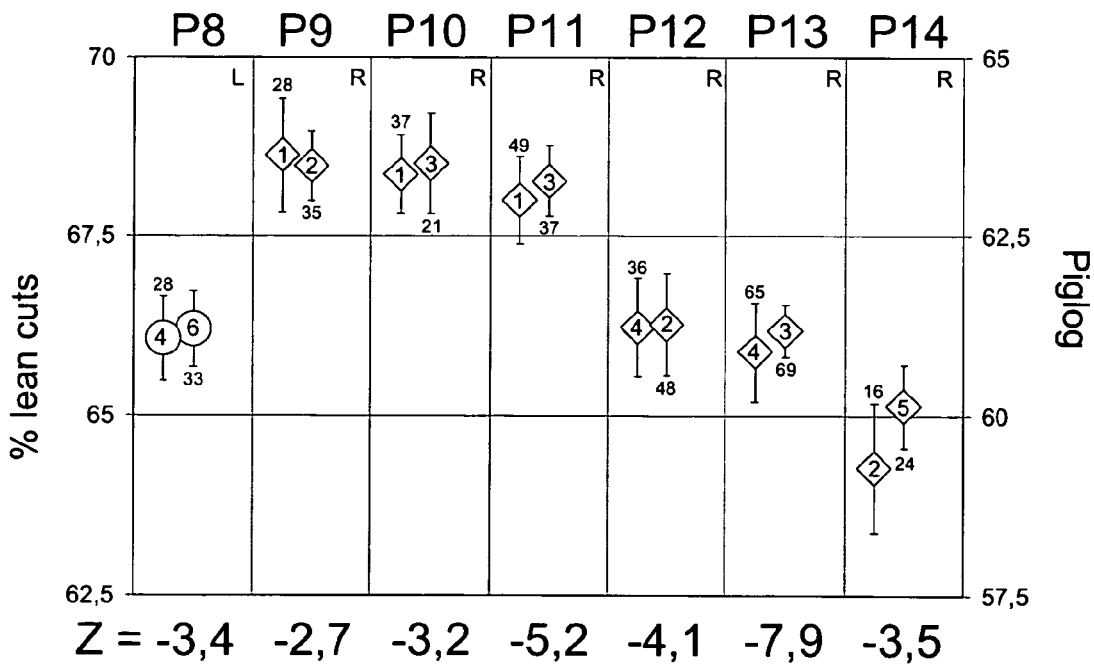

The invention is further described with the aid of the following illustrative Examples.

EXAMPLES

Example 1

Haplotype Sharing Refines the Location of an Imprinted QTL with Major Effect on Muscle Mass to a 90 Kb Chromosome Segment Containing the Porcine Igf2 Gene We herein describe the fine-mapping of an imprinted QTL with major effect on muscle mass that was previously assigned to proximal SSC2 in the pig. The proposed approach exploits linkage disequilibrium in combination with QTL genotyping by marker-assisted segregation analysis. By identifying a haplotype shared by all "Q" chromosomes and absent amongst "q" chromosomes, we map the QTL to a ≈90 Kb chromosome segment containing INS and IGF2 as only known paternally expressed genes. QTL mapping has become a preferred approach towards the molecular dissection of quantitative traits, whether of fundamental, medical or agronomic importance. A multitude of chromosomal locations predicted to harbor genes influencing traits of interest have been identified using this strategy (e.g., MacKay 2001; Andersson 2001; Flint and Mott 2001; Mauricio 2001). In most cases, however, the mapping resolution is in the order of the tens of centimorgans, which is insufficient for positional cloning of the underlying genes. High-resolution mapping of QTL, therefore, remains one of the major challenges in the genetic analysis of complex traits.

Three factors limit the achievable mapping resolution: marker density, cross-over density, and the ability to deduce QTL genotype from phenotype. Increasing marker density may still be time consuming in most organisms but is conceptually the simplest bottleneck to resolve. Two options are available to increase the local cross-over density: breed recombinants de novo or exploit historical recombination events, i.e., use linkage disequilibrium (LD). The former approach is generally used with model organisms that have a short generation time (e.g., Darvasi 1998), while the latter is the only practical alternative when working with human or large livestock species. Optimal use of LD to fine-map QTL in outbred populations is presently an area of very active research (e.g., Ardlie et al. 2002). The ability to deduce QTL genotype from phenotype can be improved by using "clones" (e.g., recombinant inbred lines) (e.g., Darvasi 1998), by means of progeny-testing (e.g., Georges et al. 1995), or by marker-assisted segregation analysis (e.g., Riquet et al. 1999).

Recently, a QTL with major effect on muscle mass and fat deposition was mapped to the centromeric end of porcine chromosome SSC2 (Nezer et al. 1999; Jeon et al. 1999). The most likely position of the QTL was shown to coincide with a chromosome region that is orthologous to HSA11p15 in the human, which is known to harbor an imprinted domain. The demonstration that the QTL was characterized by a clear parent-of-origin effect, strongly suggested that the underlying gene was imprinted and expressed only from the paternal allele. The human 11p15 imprinted domain is known to contain at least nine imprinted transcripts. Three of these are paternally expressed: LIT-1 (KVLQT1-AS), IGF2 and IGF2-AS (e.g., Reik and Walter 2001). Fifteen imprinted transcripts are known to map to the orthologous domain on distal mouse chromosome MMU7, of which four are paternally expressed: Lit-1 (Kv1qt1-as), Ins2, Igf2 and Igf2-as (e.g., worldwideweb.mgu.har.mrc.ac.uk/imprinting/imprinting.html; Onyango et al. 2000). Because of its known function in myogenesis (Florini et al. 1996), IGF2 stood out as a prime positional candidate.

To refine the map position of this QTL and to verify whether its position remained compatible with a direct role of the INS and/or IGF2 genes, we applied an approach targeting the three factors limiting the mapping resolution of QTL: (i) we generated a higher-density map of the corresponding chromosome region; (ii) we determined the QTL genotype of a number of individuals by marker-assisted segregation analysis; and (iii) we applied a LD-based haplotype sharing approach to determine the most likely position of the QTL. This approach is analogous to the one that was previously applied by Riquet et al. (1999) to refine the map position of a QTL influencing milk production in dairy cattle. It makes the assumption that the observed QTL effect is due to the segregation of a QTL allele with major substitution effect ("Q") that appeared by mutation or migration g generations ago, and swept through the populations as a result of artificial selection. As a consequence, at the present generation, n chromosomes carrying the "Q" allele are expected to share a haplotype of size≈2/ng (in Morgan) containing the QTL (Dunner et al. 1997).

By doing so, we have identified a shared haplotype spanning less than 90 Kb that is predicted to contain the Quantitative Trait Nucleotide (QTN: MacKay 2001). The corresponding chromosome segment contains INS and IGF2 as only known paternally expressed genes. This considerably enforces the candidacy of these two genes and demonstrates that LD can be exploited to map QTL in outbred populations to chromosome intervals containing no more than a handful of genes.

Materials and Methods

Pedigree Material and Phenotypic Data

The pedigree material used for this work comprised a subset of previously described Piétrain x Large White F2 pedigrees (Nezer et al., 2000; Hanset et al., 1995), as well as a series of paternal half-sib pedigrees sampled in commercial lines derived from the Piétrain and Large White breeds (Buys, personal communication). In the F2 animals, "% lean cuts" was measured as previously described (Hanset et al., 1995), while in the commercial lines % lean meat was measured as "Piglog" corresponding to (63.6882–0.4465 a –0.5096 b+0.1281 c) where a=mm back fat measured between the third and fourth lumbar vertebra at 7 cm from the spine, b=mm back fat measured between the third and fourth last rib at 7 cm from the spine, and c=mm loin thickness, measured at same position as b.

Marker-Assisted Segregation Analysis

The QTL genotype of each sire was determined from the Z-score, corresponding to the log 10 of the likelihood ratio $L_{H_1}/L_{H_0}$, where $L_{H_1}$ corresponds to the likelihood of the pedigree data assuming that the boar is of "Qq" genotype, and $L_{H_0}$ corresponds to the likelihood of the pedigree data assuming that the boar is of "QQ" or "qq" genotype. The corresponding likelihoods were computed as:

$$L = \prod_{i=1}^{n} \frac{1}{\sqrt{2\pi}\sigma} e^{\frac{-(y_i - (\bar{y} \pm a))^2}{2\sigma^2}}$$

In this, n is the number of informative offspring in the corresponding pedigree, $y_i$ is the phenotype of offspring i, $\bar{y}$ is the average phenotype of the corresponding pedigree computed over all (informative and non-informative) offspring, σ is the residual standard deviation maximizing L, and a is the Q to q allele substitution effect. a was set at zero when computing $L_{H_0}$, and at +1% for "R" offspring and –1% for "L" offspring when computing $L_{H_1}$ (Nezer et al. 1999).

Boars were considered to be "Qq" when Z>2, "QQ" or "qq" when Z<–2 and of undetermined genotype if 2>Z>–2.

Linkage Disequilibrium Analysis

Probabilities for two chromosomes to be identical-by-descent (IBD) at a given map position conditional on flanking marker data were computed according to Meuwissen and Goddard (2001). The effective population size ($N_e$) was set at 200 based on estimates of $N_e$ determined from LD data (Harmegnies, unpublished observations), and the number of generations to the base population at 20. A multipoint test for association was performed using the DISMULT program described in Terwilliger 1995.

Results

QTL genotyping by marker-assisted segregation analysis: We genotyped a series of paternal half-sib families counting at least 20 offspring for two microsatellite markers located on the distal end of chromosome SSC2 and spanning the most likely position of the imprinted QTL: SWR2516 and SWC9 (Nezer et al. 1999; Jeon et al. 1999). These families originated either from a previously described Piétrain x Large White F2 pedigree (Nezer et al. 2002), or from two composite pig lines derived from Large White and Piétrain founder animals (Nadine Buys, personal communication).

The pedigrees from sires that were heterozygous for one or both of these markers were kept for further analysis. Twenty such pedigrees could be identified for a total of 941 animals. Offspring were sorted in three classes based on their marker genotype: "L" (left homologue inherited from the sire), "R" (right homologue inherited from the sire), or "?" (not informative or recombinant in the SWR2516-SWC9 interval).

Offspring were slaughtered at a constant weight of approximately 105 Kgs, and a series of phenotypes collected on the carcasses including "% lean meat," measured either as "% lean cuts" (experimental cross) or as "Piglog" (composite lines) (see Materials and Methods).

We then computed the likelihood of each sire family under two hypotheses: $H_0$, postulating that the corresponding boar was homozygous at the QTL, and $H_1$ postulating that the boar was heterozygous at the QTL. Assuming a bi-allelic QTL, $H_0$ corresponds to QTL genotypes "QQ" or "qq," and $H_1$ to genotype "Qq." Likelihoods were computed using "% lean meat" as phenotype (as the effect of the QTL was shown to be most pronounced on this trait in previous analyses), and assuming a Q to q allele substitution effect of 2.0% (Nezer et al. 1999). If the odds in favor of one of the hypotheses were superior or equal to 100:1, the most likely hypothesis was considered to be true. Results are expressed as lod scores (z): the $\log_{10}$ of the likelihood ratio $H_1/H_0$. Boars were considered to be of heterozygous "Qq" genotype if z was superior to 2, of homozygous "QQ" or "qq" genotype if z was inferior to –2, and of undetermined QTL genotype if –2<z<2.

Using these rules, we could determine the QTL genotype for fourteen of the twenty boars. Seven of these proved to be heterozygous "Qq," the other seven to be homozygous and thus either of "QQ" or "qq" genotype (FIG. 1). Constructing a physical and genetic map of the porcine orthologue of the human 11p15 imprinted domain:

The SWC9 marker was known from previous studies to correspond to a (CA), microsatellite located in the 3'UTR of the porcine IGF2 gene (Nezer et al. 1999; Jeon et al. 1999; Amarger et al. 2002). We performed a BLAST search with the sequence of the porcine SWR2516 marker (gi|7643973|) against the sequence contigs spanning the human 11p15 imprinted domain worldwideweb.ensembl.org/Homo_sapiens/. A highly significant similarity (expected value of $6\times10^{-5}$ calculated based on the size of the NCBI "nr" database) was found between SWR2516 and sequence contig AC001228 (gi|1935053|) at 3.3 Kb of the p57 gene. This suggested that the SWR2516-SWC9 marker interval in the pig might correspond to the p57-IGF2 interval of the human 11p15 imprinted domain.

We then developed porcine sequence tagged sites (STS) across the orthologous region of the human 11p15 imprinted domain. Sixteen of these were developed in genes (TSSC5, CD81, KVLQT1 (3x), TH (2x), INS (3x), IGF2 (3x), H19 (3x)), and five in intergenic regions ($IG_{IGF2-H19}$, $IG_{H19-RL23mrp}$(4x)). The corresponding primer sequences were derived from the porcine genomic sequence when available (Amarger et al. 2002), or from porcine-expressed sequence tags (EST) that were identified by BLAST searches using the human orthologues as query sequences (Table 1).

We screened a porcine BAC library (Fahrenkrug et al. 2001) by filter hybridization using (i) human cDNA clones corresponding to genes known to map to 11p15, as well as (ii) some of the 21 previously described porcine STS. Seven of the identified BACs were shown by PCR to contain at least one of the porcine STS available in the region and were kept for further analysis together with two BACs that were previously shown to span the TH-H19 region (Amarger et al. 2002). Three additional STS were developed from BAC end sequences (389B2T7, 370C17T7, 370SP6). 370SP6 revealed a highly significant BLAST hit (expected value $10^{-7}$) downstream from the ASCL2 gene providing an additional anchor point between the human and porcine sequence. Using STS content mapping, we assembled the BAC contig shown in FIG. 2. It confirms the overall conservation of gene order between human and pigs in this chromosome region and indicates that the gap remaining in the human sequence between the INS and ASCL2 genes may not be larger than 55 Kb.

All available STS were then amplified from genomic DNA of the fourteen QTL genotyped boars (see above) and cycle-sequenced in order to identify DNA sequence polymorphisms. We identified a total of 43 SNPs: two in TSSC5, fifteen in KVLQT1, three in 389B2-T7, four in TH, seven in INS, four in IGF2, one in $IG_{(IGF2-H19)}$, three in H19 and four in $IG_{(H19-RL23MRP)}$ (Table 1).

Three microsatellites were added to this marker list: one (KVLQT1-SSR) isolated from BAC 956B11 and two (PULGE1 and PULGE3) isolated from BAC 370.

Assembling Pools of "Q" Versus "q" Bearing Chromosomes:

To reconstruct the marker linkage phase of the fourteen QTL genotyped sires, we selected—for each boar—offspring that were homozygous for the alternate paternal SWR2516-SWC9 haplotypes. These were genotyped for all SNPs and microsatellites available in the region, and from these genotypes we manually determined the linkage phase of the boars.

Figure 2:
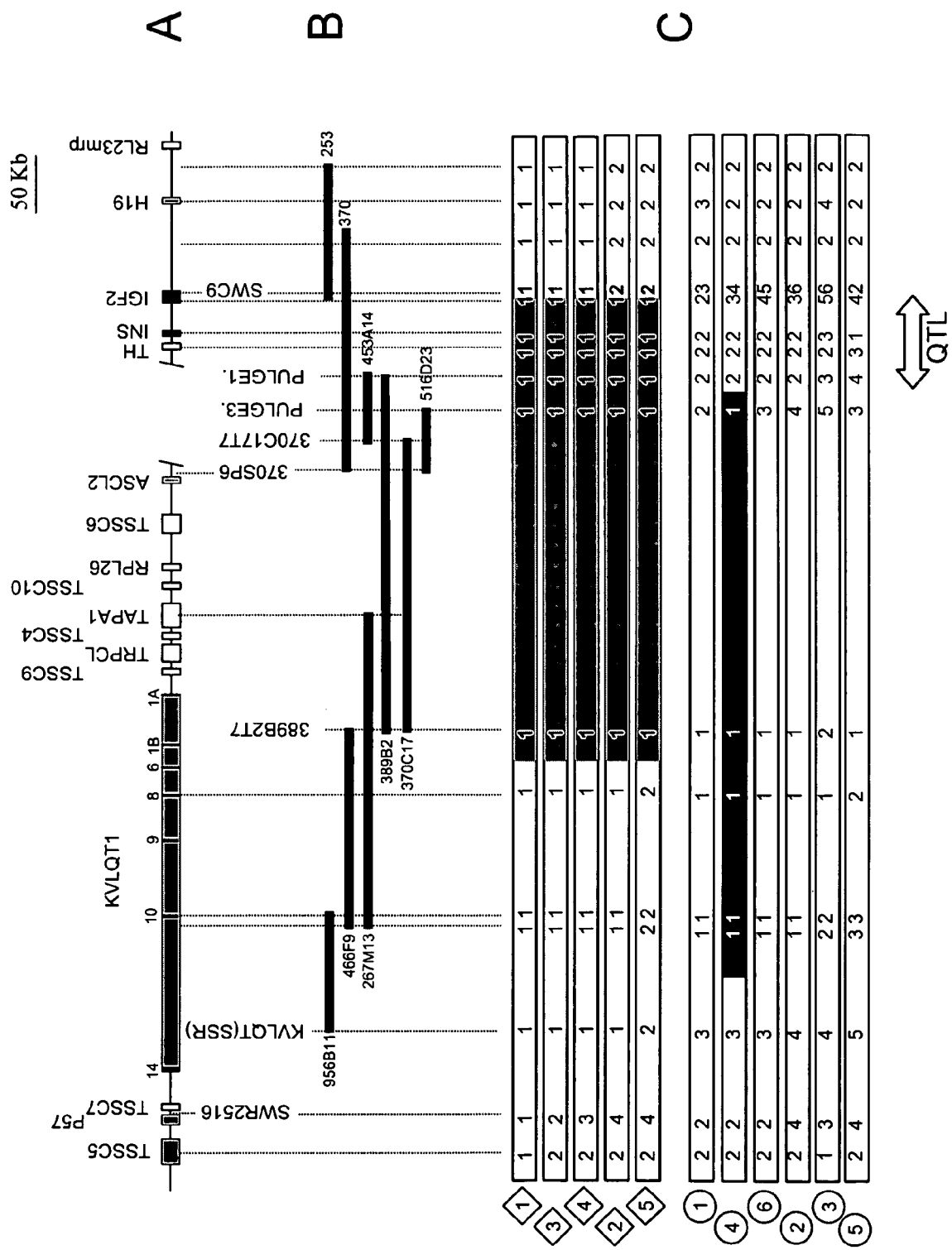
FIG. 2: A. Schematic representation of the human 11p15 imprinted domain according to Onyango et al. (2000). B. BAC contig spanning the porcine orthologue of the 11p15 imprinted domain, assembled by STS content mapping. The length of the horizontal bars does not reflect the actual physical size of the corresponding BACs. C. Marker haplotypes of the five "Q" chromosomes (diamonds) and six "q" chromosomes (circles). Closely linked SNPs (<5 kb) were merged into poly-allelic multisite haplotypes (cfr. Table 2). The chromosome segments highlighted in green correspond to the haplotype shared by all "Q" chromosomes and therefore assumed to contain the QTL. The chromosome segment highlighted in red corresponds to a haplotype shared by chromosome "q4" and chromosomes "$Q^{1-4}$," which, therefore, excludes the QTL out of this region. The resulting most likely position of the QTL is indicated by the arrow.

For six of the seven boars, shown by marker-assisted segregation analysis to be of "Qq" genotype (FIG. 1), the "Q" chromosomes associated with an increase in % lean meat proved to be identical-by-state (IBS) over their entire length. This haplotype was, therefore, referred to as "$Q^1$." The haplotype corresponding to the seventh "Q" chromosome (P7 in FIG. 2) was different and referred to as "$Q^2$." For three of these sires, the haplotypes associated with a decrease in % lean meat proved to be completely IBS as well, and were thus referred to as "$q^1$." The other four "q" chromosomes carried distinct haplotypes, and were referred to as "$q^2$," "$q^3$," "$q^4$" and "$q^5$" (FIG. 2). The first boar that proved to be homozygous for the QTL by marker-assisted segregation analysis (P8) carried the "$q^4$" haplotype on one if its chromosomes. Its other haplotype, therefore, had to be of "q" genotype as well and was referred to as "$q^6$."

Boar P9 appeared to be heterozygous "$Q^1/Q^2$." Boars P10 and P11 carried the "$Q^1$" haplotype shared by six of the "Qq" boars. As a consequence, the other chromosomes of boars P10 and P11, which were IBS as well, were placed in the "Q" pool and referred to as "$Q^3$." Homozygous boar P12 carried haplotype "$Q^2$." As a consequence, its homologue was referred to as "$Q^4$." Following the same recursive procedure, boars P13 and P14 were identified as being, respectively, "$Q^3Q^4$" and "$Q^2Q^5$."

The marker genotypes of the resulting five "Q" and five "q" chromosomes are shown in FIG. 2. In this figure, closely linked (<5 Kb) SNPs were merged into a series of polyallelic multisite haplotypes. The correspondence between SNP genotype and haplotype number is given in Table 2.

All "Q" chromosomes share a ≈90 Kb common haplotype encompassing the INS and IGF2 genes not present in the "q" chromosomes. Visual examination of the "Q" and "q" pools immediately reveals that all five chromosomes in the "Q" pool indeed share an IBS haplotype spanning the 389B2T7-IGF2 interval (FIG. 2). Four of the five "Q" chromosomes ("$Q^1$," "$Q^2$," "$Q^3$" and "$Q^4$") also carry a common haplotype in the proximal KVLQT1(I12)-(I7) interval, while the fifth one ("$Q^5$") carries a completely different KVLQT1(I12)-(I7) haplotype. This strongly suggests an ancestral recombination between KVLQT1(I7) and 389B2T7. Likewise, three of the five "Q" chromosomes ("$Q^1$," "$Q^3$," "$Q^4$") carry the same haplotype distal from IGF2, while the two remaining ones ("$Q^2$," "$Q^5$") are sharing a completely distinct one. Again, this is best explained by assuming an ancestral recombination event just proximal from the SWC9 microsatellite marker.

These observations, therefore, strongly suggest that the hypothesized "Q" allele associated with an increase in "% lean meat" appeared by mutation or migration on a founder chromosome carrying the haplotype highlighted in FIG. 2, and that the QTL is located in the KVLQT1(I7)-SWC9 interval. At present, our best estimate of the size of this interval is of the order of 500 Kb (FIG. 2).

Figure 3:
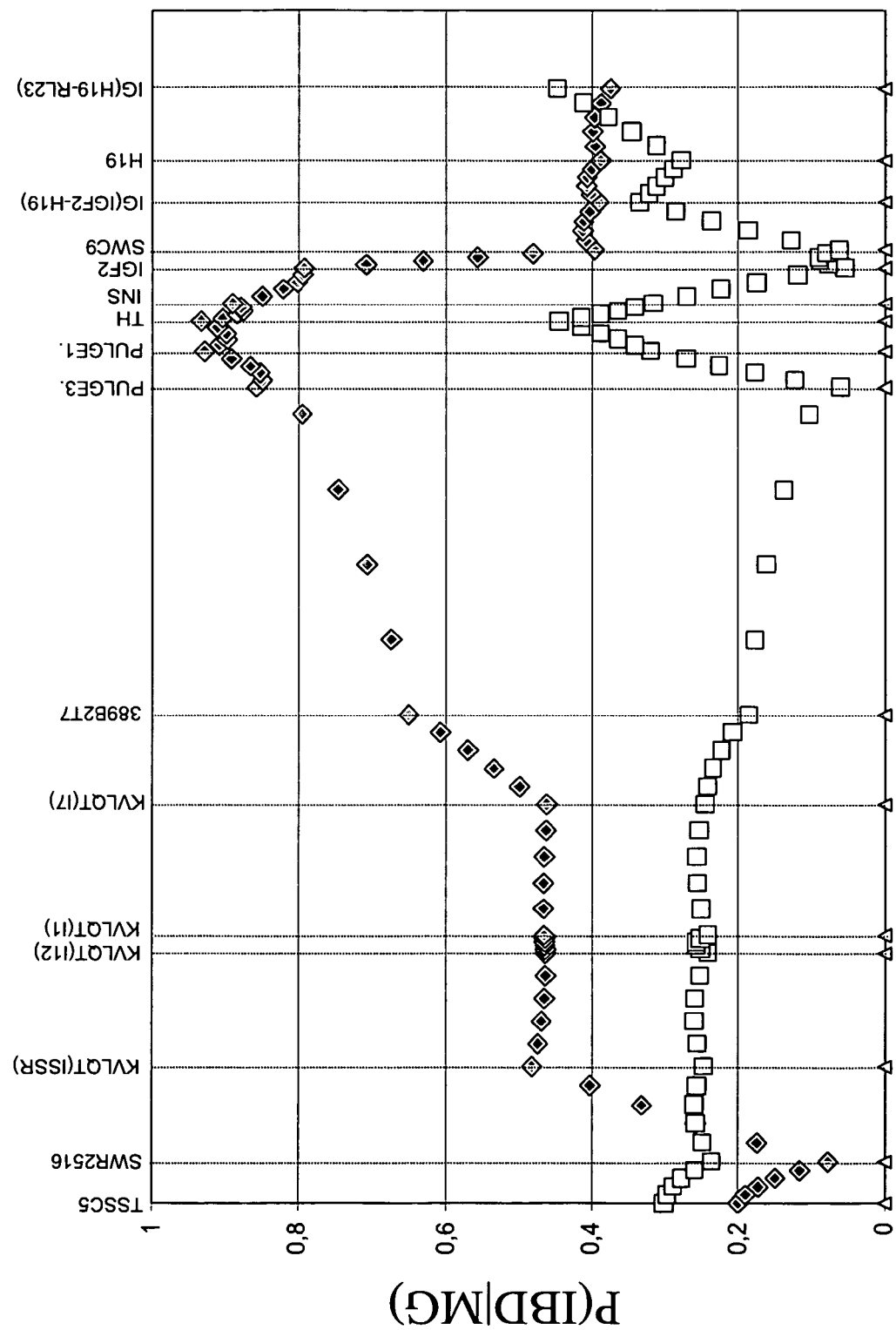
FIG. 3: Average probability for two chromosomes to be identical-by-descent at a given map position conditional on flanking marker data (p(IBD|MG)), along the chromosome segment encompassing the p57-H19 imprinted domain, computed according to Meuwissen and Goddard (2001). The positions of the markers defined according to Tables 1 and 2 are shown by the vertical dotted lines.

No such shared haplotype could be identified in the "q" pool. As expected under our model, the "q" pool exhibited a higher level of genetic diversity. The "q" bearing chromosomes would indeed be older, having had ample opportunity to recombine, thereby increasing haplotype diversity. This can be quantified more accurately by computing the average pair-wise probability for "Q" and "q" chromosomes to be IBD conditional on flanking marker data, using the coalescent model developed by Meuwissen and Goddard (2001). As shown in FIG. 3, the average pair-wise IBD probability amongst the five "Q" chromosomes is superior to 0.4 over the entire KVLQT1(SSR)-$IG_{(H19-RL23mrp)}$ interval and exceeds 0.9 in the PULGE3-IGF2 interval. For the "q" chromosomes, the equivalent parameter averages 0.25 in the same region. It is worthwhile noting, however, that even amongst "q" chromosomes, the average pair-wise IBD probability peaks just above 0.4 between TH and INS, which is thought to reflect a "q"-specific haplotype signature.

It is noteworthy that chromosome "$q^4$" carries a KVLQT1 (I12)-PULGE3 haplotype that is IBS with the ancestral "Q" haplotype in the KVLQT1(I12)-PULGE3 interval. The probability that this IBS status reflects IBD was estimated at ≈0.50 using the coalescent model of Meuwissen and Goddard (2001). Assuming IBD, this would position the QTL in the PULGE3-SWC9 interval, measuring less than 90 Kb and containing TH, INS and IGF2 as only known genes.

One could argue that the probability to identify a shared haplotype amongst five chromosomes by chance alone is high and does not support the location of the QTL within this region. To more quantitatively estimate the significance of the haplotype sharing amongst "Q" chromosomes, accounting for the distance between adjacent markers as well as allelic frequencies, we, therefore, performed a multipoint LD analysis using the DISMULT program (Terwilliger 1995). To test the significance of the haplotype sharing observed amongst the five "Q" chromosomes, we performed the same DISMULT analysis on all 462 possible combinations of the 11 chromosomes taken five at a time. For each of these analyses, we stored the highest likelihood obtained anywhere along the analyzed chromosome segment. The likelihood obtained using the real five "Q" chromosomes at the position of marker PULGE3 was the highest one obtained across all chromosome permutations (data not shown), clearly indicating that the observed haplotype sharing is very unlikely to be fortuitous.

When we previously demonstrated that only the paternal SSC2 QTL allele influenced muscle mass and that the most likely QTL position coincided with IGF2, this gene obviously stood out as the prime candidate (Nezer et al. 1999; Jeon et al. 1999). On the basis of the initial linkage analysis, however, the confidence interval for the QTL covered approximately 4 cM, which were bound to contain a multitude of genes other than IGF2. It was, therefore, useful to corroborate these papers by refining the map position of the QTL, which we set out to do by exploiting both LD and marker-assisted segregation analysis. Because of the observed parent-of-origin effect, we focused our analysis on a chromosome region that is the ortholog of the human 11p15 imprinted domain. We herein provide strong evidence that the QTL indeed maps to the p57-H19 imprinted gene cluster, and within this region to a chromosome segment of ≈90 Kb known to contain the TH, INS and IGF2 genes. These findings, therefore, considerably strengthen the candidacy of IGF2, and justify a detailed analysis of this gene.

The fact that we succeeded in refining the map position of this QTL down to the subcentimorgan level, supports its simple molecular architecture. Together with recent successes in positional cloning and identification of the mutations that underlie QTL (e.g., Grobet et al. 1997; Milan et al. 2001; Grisart et al. 2002; Blott et al. 2002), this clearly indicates that at least part of the genetic variation of production traits in livestock is due to single mutations with large effects on the traits of interest.

The success of haplotype sharing approaches in fine-mapping QTL in livestock also suggests that QTL may be mapped in these populations by virtue of the haplotype signature resulting from intense selection on "Q" alleles, i.e., haplotypes of unusual length given their population frequency. The feasibility of this approach has recently been examined in human populations for loci involved in resistance to malaria (Sabeti et al. 2002). QTL could thus be identified in livestock in the absence of phenotypic data.

Example 2

Positional Identification of a Regulatory Mutation in IGF2 Causing a Major QTL Effect on Muscle Development in the Pig The identification of causative mutations for Quantitative Trait Loci (QTLs) is a major hurdle in genetic studies of multifactorial traits and disorders. Here, we show that a paternally expressed QTL affecting muscle mass and fat deposition in pigs is caused by a single nucleotide substitution in intron 3 of IGF2. The mutation occurs in an evolutionary conserved CpG island that is hypomethylated in skeletal muscle. Pigs carrying the mutation have a three-fold increase in IGF2 mRNA expression in postnatal muscle. The mutation abrogates in vitro interaction with a nuclear factor, most likely a repressor. The mutation has experienced a selective sweep in several pig breeds. The study provides an outstanding example where the causal relationship between a regulatory mutation and a QTL effect has been established.

The imprinted IGF2-linked QTL is one of the major porcine QTLs for body composition. It was first identified in intercrosses between the European Wild Boar and Large White domestic pigs and between Piétrain and Large White pigs.[1, 2] The data showed that alleles from the Large White and Piétrain breed, respectively, were associated with increased muscle mass and reduced back-fat thickness, consistent with the existing breed-differences in the two crosses. A paternally expressed IGF2-linked QTL was subsequently documented in intercrosses between Chinese Meishan and Large White/Landrace pigs[3] and between Berkshire and Large White pigs.[4] In both cases, the allele for high muscle mass was inherited from the lean Large White/Landrace breed.

We have recently used a haplotype sharing approach to refine the map position of the QTL.[5] We assumed that a new allele (Q) promoting muscle development occurred g generations ago on a chromosome carrying the wild-type allele (q). We also assumed that the favorable allele has gone through a selective sweep due to the strong selection for lean growth in commercial pig populations. Twenty-eight chromosomes with known QTL status were identified by marker-assisted segregation analysis using cross-bred Piétrain and Large White boars. All 19 Q-bearing chromosomes shared a haplotype in the 90 kilobase pairs (kb) interval between the microsatellites PULGE1 and SWC9 (IGF2 3'-UTR), which was not present among the q chromosomes and was, therefore, predicted to contain the QTL. In contrast, the nine q chromosomes exhibited six distinct marker haplotypes in the same interval. This region is part of the CDKN1C-H19 imprinted domain and contains INS and IGF2 as the only known paternally expressed genes. Given the known functions of these genes and especially the role of IGF2 in myogenesis,[6] they stood out as prime positional candidates. A comparative sequence analysis of the porcine INS-IGF2 region revealed as many as 59 conserved elements (outside known exons) between pig and human, all being candidate regions for harboring the causative mutation.[7]

Figure 4A:
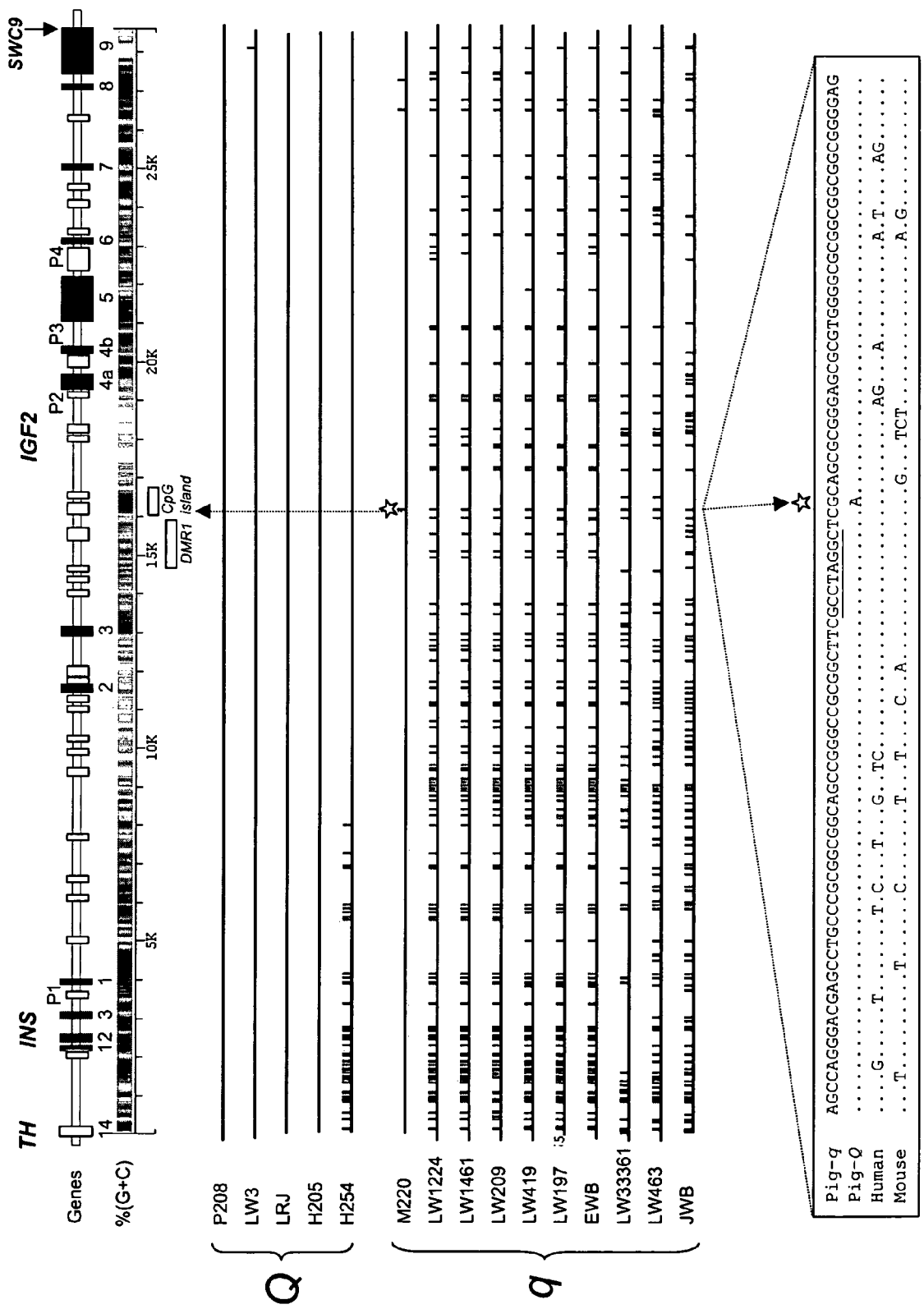
FIG. 4A: DNA sequence polymorphisms identified in a 28.6 kb segment spanning the porcine TH (exon 14), INS and IGF2 genes. The average (C+G) content of a moving 100-bp window is shown on a gray scale (black 100%, white 0%). The positions of evolutionary conserved regions,[7] including the DMR1 and associated CpG island in IGF2 intron 3, are marked by horizontal cylinders. The Viewgene program[25] was used to highlight the 258 differences between the reference Q P208 sequence, four Q, and ten q chromosomes. The position of the causative intron3-nt3072G→A mutation is marked by an asterisk. The sequence context of the conserved footprint surrounding intron3-nt3072 is shown for pig (pig-q (SEQ ID NO: 115) and pig-Q (SEQ ID NO: 116)), human (SEQ ID NO: 117), and mouse (SEQ ID NO: 118). The conserved palindromic octamer sequence is underlined. P=Piétrain; LW=Large White; LR=Landrace; H=Hampshire; M=Meishan; EWB=European Wild Boar; JWB=Japanese Wild Boar.
Figure 4B:
FIG. 4B: Neighbor-Joining tree of 18,560 bp of the porcine IGF2 gene based on 15 sequences classified as representing q and Q alleles. The analysis was restricted to the region from IGF2 intron 1 to SWC9 in the 3'UTR to avoid problems with the presence of recombinant haplotypes. The tree was constructed using MEGA version 2.1[26] and positions with insertions/deletions were excluded. Bootstrap values (after 1000 replicates) are reported on the nodes.

In order to identify the causative mutation, we re-sequenced one of the 19 Q-chromosomes (P208) and six q-chromosomes (each corresponding to one of the six distinct marker haplotypes) for a 28.6 kb segment containing IGF2, INS, and the 3' end of TH. This chromosome collection was expanded by including Q- and q-chromosomes from (i) a Wild Boar/Large White intercross segregating for the QTL,[2] (ii) a Swedish Landrace boar showing no evidence for QTL segregation in a previous study,[8] (iii) $F_1$ sires from a Hampshire/Landrace cross showing no indication for QTL segregation,[9] and (iv) an $F_1$ sire from a Meishan/Large White intercross. A Japanese Wild Boar was included as a reference for the phylogenetic analysis; the QTL status of this animal is unknown but we assume that it is homozygous wild-type (q/q). We identified a total of 258 DNA sequence polymorphisms corresponding to a staggering one polymorphic nucleotide per 111 base pairs (bp) (FIG. 4A). The sequences formed three major and quite divergent clusters (FIG. 4B). The only exception to this pattern was one Hampshire haplotype (H254) that was apparently recombinant.

The two established Q haplotypes from Piétrain and Large White animals (P208 and LW3) were identical to each other and to the chromosomes from the Landrace (LRJ) and Hampshire/Landrace (H205) animals for almost the entire region, showing that the latter two must be of Q-type as well. The absence of QTL segregation in the offspring of the $F_1$ Hampshire×Landrace boar carrying the H205 and H254 chromosomes implies that the latter recombinant chromosome is also of Q-type. This places the causative mutation downstream from IGF2 intron 1, the region for which H254 is identical to the other Q chromosomes. The Large White chromosome (LW197) from the Meishan/Large White pedigree clearly clustered with q chromosomes, implying that the $F_1$ sire used for sequencing was homozygous q/q as a previous QTL study showed that the Meishan pigs carried an IGF2 allele associated with low muscle mass.[3] Surprisingly, the Meishan allele (M220) was nearly identical to the Q chromosomes but with one notable exception, it shared a G nucleotide with all q chromosomes at a position (IGF2-intron3-nt3072) where all Q chromosomes have an A nucleotide (FIG. 4A).

Under a bi-allelic QTL model, the causative mutation would correspond to a DNA polymorphism for which the two alleles segregate perfectly between Q- and q-chromosomes. The G to A transition at IGF2-intron3-nt3072 is the only polymorphism fulfilling this criterion, implying that it is the causative Quantitative Trait Nucleotide (QTN).[10] We have so far tested 12 large sire families where the sire is heterozygous AG at this position and all have showed evidence for QTL segregation. In contrast, we have tested more than 40 sires, representing several different breeds, genotyped as homozygous A/A or G/G at this position without obtaining any significant evidence for the segregation of a paternally expressed QTL at the IGF2 locus. The results provide conclusive genetic evidence that IGF2-intron3-nt3072G→A is the causative mutation.

Figure 5A:
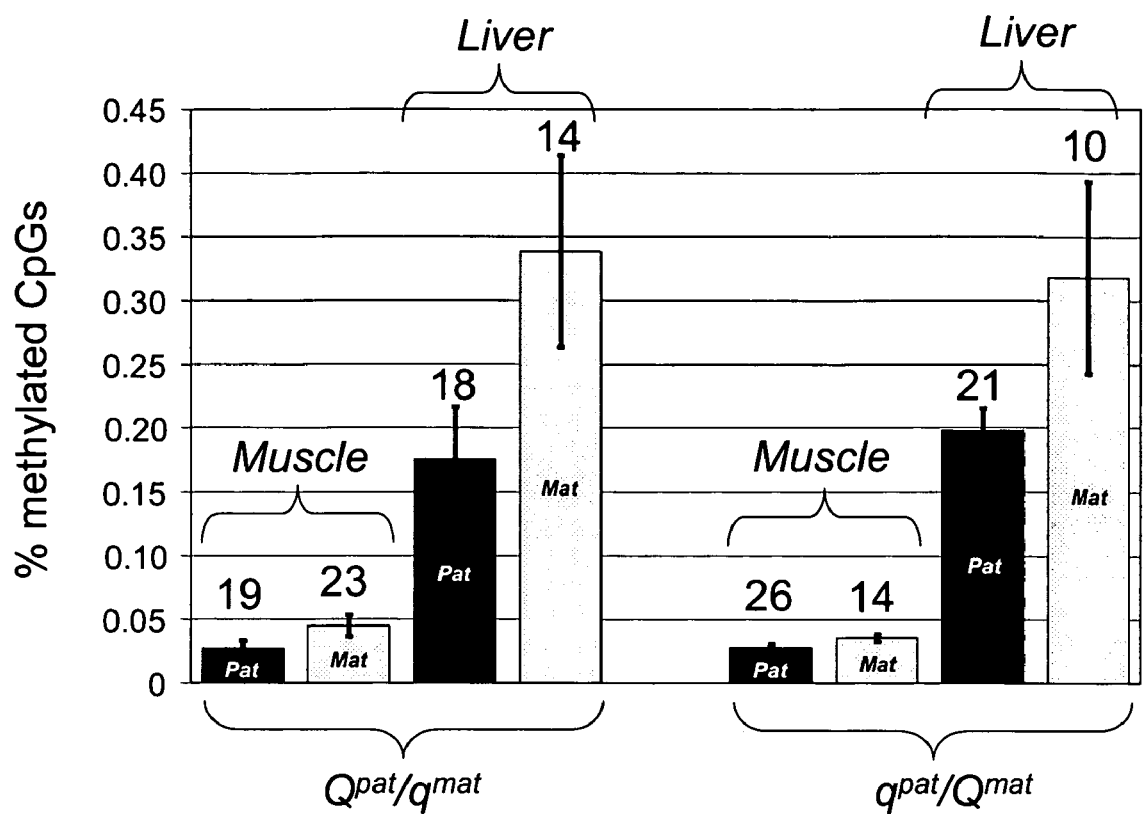
FIG. 5A: Percentage methylation determined by bisulphite sequencing for the 300 bp fragment centered on intron3-nt3072, containing 50 CpG dinucleotides, in liver and skeletal muscle of four-month-old $Q^{pat}/q^{mat}$ and $q^{pat}/Q^{mat}$ individuals. The number of analyzed chromosomes as well as the standard errors of the estimated means are given. Pat and Mat refer to the paternal and maternal alleles, respectively, determined based on the intron3-nt3072G→A mutation.

IGF2-intron3-nt3072 is part of an evolutionary conserved CpG island of unknown function,[7] located between Differentially Methylated Region 1 (DMR1) and a matrix attachment region previously defined in mice.[11-13] The 94 bp sequence around the mutation shows about 85% sequence identity to both human and mouse, and the wild-type nucleotide at IGF2-intron3-nt3072 is conserved among the three species (FIG. 4A). The QTN occurs three bp downstream of an eight bp palindrome also conserved between the three species. The methylation status of the 300 bp fragment centered on IGF2-intron3-nt3072 and containing 50 CpG dinucleotides was examined by bisulphite sequencing in four month old $Q^{pat}/q^{mat}$ and $q^{pat}/Q^{mat}$ animals. In skeletal muscle, paternal and maternal chromosomes were shown to be essentially unmethylated (including the IGF2-intron3-nt3071 C residue) irrespective of the QTL genotype of the individual (3.4% of CpGs methylated on average; FIG. 5A). The CpG island was more heavily and also differentially methylated in liver, 33% of the CpGs were methylated on the maternal alleles versus 19% on the paternal allele. Unexpectedly, therefore, this CpG island behaves as a previously unidentified DMR in liver, the repressed maternal allele being more heavily methylated than the paternal allele, which is the opposite of what is documented for the adjacent DMR1 in the mouse.

Figure 5B:
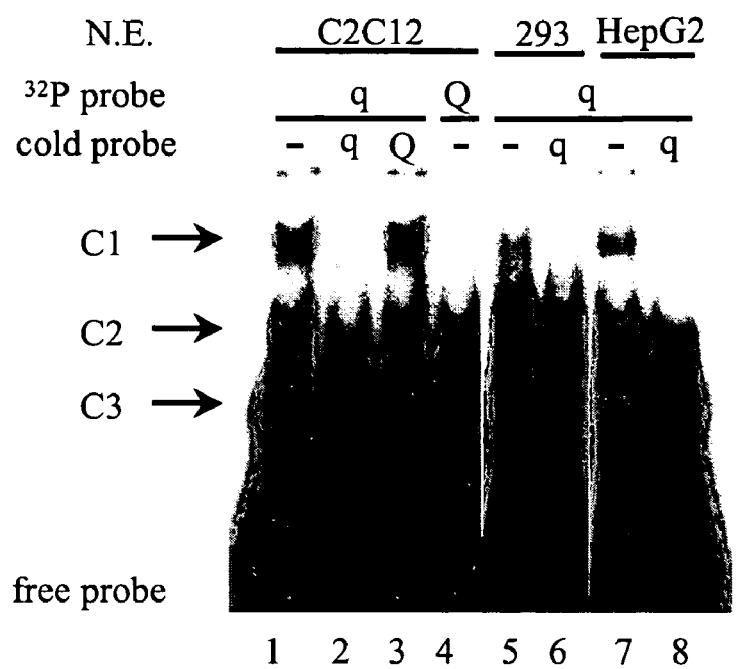
FIG. 5B: Electrophoretic mobility shift analyses (EMSA) using 10 µg nuclear extracts (N.E.) from mouse C2C12 myoblast cells, human HEK293 embryonic kidney cells, and human HepG2 hepatocytes. The q and Q oligonucleotide probes corresponded to the wild-type and mutant sequences, respectively. Competition was carried out with a 50-fold excess of cold nucleotide. Complex 1 (C1) was specific and exclusively detected with the q probe. C2 was also specific and stronger in q but probably present also with the Q probe. C3 was unspecific.

To uncover a possible function for this element, we performed electrophoretic mobility shift analyses (EMSA) using oligonucleotide probes spanning the QTN and corresponding to the wild-type (q) and mutant (Q) sequences. Nuclear extracts from murine C2C12 myoblast cells, human HEK293 cells, and human HepG2 cells were incubated with radioactively labeled q or Q oligonucleotides. One specific band shift (complex C1 in FIG. 5B) was obtained with the wild-type (q) but not the mutant (Q) probe using extracts from C2C12 myoblasts; similar results were obtained using both methylated and unmethylated probes. A band shift with approximately the same migration, but weaker, was also detected in extracts from HEK293 and HepG2 cells. The specificity of the complex was confirmed since competition was obtained with ten-fold molar excess of unlabeled q probe, whereas a 50-fold excess of unlabeled Q probe did not achieve competition (FIG. 5B). Thus, the wild-type sequence binds a nuclear factor, and this interaction is abrogated by the mutation.

Figure 5C:
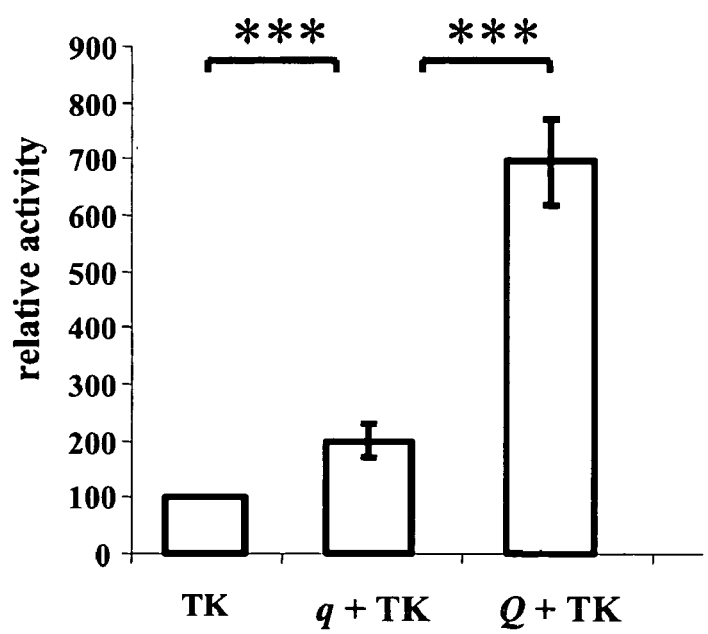
FIG. 5C: Luciferase assays of reporter constructs using the TK promoter. The pig IGF2 fragments (Q and q) contained 578 bp from intron 3 (nucleotide 2868 to 3446) including the causative G to A transition at nucleotide 3072. The relative activities compared with the basic TK-LUC vector are reported as means±standard errors based on triplicate experiments. A student's t-test revealed highly significant differences for all pair-wise comparisons; ***=P<0.001.
Figure 7:
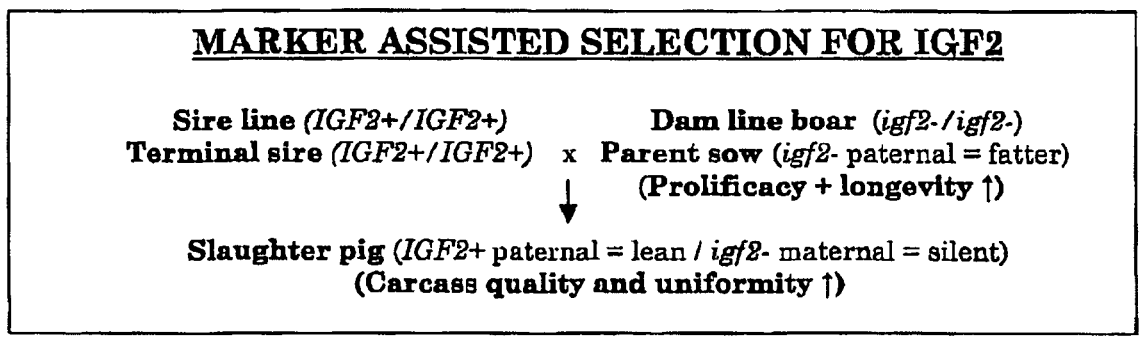
FIG. 7: Representation of a suitable marker-assisted selection program for the IGF2 mutation.

To further characterize the functional significance of the IGF2 Q mutation, we studied its effect on transcription by employing a transient transfection assay in mouse C2C12 myoblasts. We made Q and q constructs containing a 578 bp fragment from the actual region inserted in front of a Luciferase reporter gene driven by the herpes thymidine kinase (TK) minimal promoter. The two constructs differed only by the IGF2-intron3-nt3072G→A transition. The ability of the IGF2 fragments to activate transcription from the heterologous promoter was compared with the activity of the TK-promoter alone. The presence of the q-construct caused a two-fold increase of transcription, whereas the Q-construct caused a significantly higher, seven-fold, increase (FIG. 5C). Our interpretation of this result, in light of the results from the EMSA experiment, is that the Q mutation abrogates the interaction with a repressor protein that modulates the activity of a putative IGF2 enhancer present in this CpG island. This view is consistent with our in silico identification of potential binding sites for both activators and repressors in this intronic DNA fragment.[14]

The in vivo effect of the mutation on IGF2 expression was studied in a purpose-built Q/q×Q/q intercross counting 73 offspring. As a deletion encompassing DMR0, DMR1, and the associated CpG island derepresses the maternal IGF2 allele in mesodermal tissues in the mouse,[12] we tested the effect of the intron3-nt3072 mutation on IGF2 imprinting in the pig. This was achieved by monitoring transcription from the paternal and maternal IGF2 alleles in tissues of q/q, $Q^{pat}/q^{mat}$, and $q^{pat}/Q^{mat}$ animals that were heterozygous for the SWC9 microsatellite located in the IGF2 3'UTR. Imprinting could not be studied in Q/Q animals, which were all homozygous for SWC9. Before birth, IGF2 was shown to be expressed exclusively from the paternal allele in skeletal muscle and kidney, irrespective of the QTL genotype of the fetuses. At four months of age, weak expression from the maternal allele was observed in skeletal muscle, however, at comparable rates for all three QTL genotypes (FIG. 6, Panel A). Only the paternal allele could be detected in four-month-old kidney (data not shown). Consequently, the mutation does not seem to affect the imprinting status of IGF2. The partial derepression of the maternal allele in skeletal muscle of all QTL genotypes may, however, explain why in a previous study muscular development was found to be slightly superior in $q^{pat}/Q^{mat}$ versus q/q animals, and in Q/Q versus $Q^{pat}/q^{mat}$ animals.[2]

The Q allele was expected to be associated with an increased IGF2 expression since IGF2 stimulates myogenesis.[6] To test this, we monitored the relative mRNA expression of IGF2 at different ages in the Q/q×Q/q intercross using both Northern blot analysis and real-time PCR (FIG. 6, Panels B and C). The expression levels in fetal muscle and postnatal liver was about ten-fold higher than in postnatal muscle. No significant difference was observed in fetal samples or in postnatal liver samples, but a significant three-fold increase of postnatal IGF2 mRNA expression in skeletal muscle was observed in (Q/Q or $Q^{pat}/q^{mat}$) versus ($q^{pat}/Q^{mat}$ or q/q) progeny. The significant difference in IGF2 expression revealed by real-time PCR was confirmed using two different internal controls, GAPDH (FIG. 6, Panel C) and HPRT.[15] We found an increase of all detected transcripts originating from the three promoters (P2-P4) located downstream of the mutated site. Combined, these results provide strong support for IGF2 being the causative gene. The lack of significant differences in IGF2 mRNA expression in fetal muscle and postnatal liver are consistent with our previous QTL study showing no effect of the IGF2 locus on birth weight and weight of liver.(2)

There has been a strong selection for lean growth (high muscle mass and low fat content) in commercial pig populations in Europe and North America during the last 50 years. Therefore, we investigated how this selection pressure has affected the allele frequency distribution of the IGF2 QTL. The causative mutation was absent in a small sample of European and Asian Wild Boars and in several breeds that have not been strongly selected for lean growth (Table 1). In contrast, the causative mutation was found at high frequencies in breeds that have been subjected to strong selection for lean growth. The only exceptions were the experimental Large White population at the Roslin Institute that was founded from commercial breeding stock in the UK around 1980,[16] as well as the experimental Large White populations used for the Piétrain/Large White intercross;[1] these two populations thus reflect the status in some commercial populations about 20 years ago and it is possible that the IGF2*Q allele is even more predominant in contemporary populations. The results demonstrate that IGF2*Q has experienced a selective sweep in several major commercial pig populations and it has apparently been spread between breeds by cross-breeding.

The results have important practical implications. The IGF2*Q mutation increases the amount of meat produced, at the expense of fat, by 3 to 4 kg for an animal slaughtered at the usual weight of about 100 kg. The high frequency of IGF2*Q among major pig breeds implies that this mutation affects the productivity of many millions of pigs in the Western world. The development of a simple diagnostic DNA test now facilitates the introgression of this mutation to additional breeds. This could be an attractive way to improve productivity in local breeds as a measure to maintain biological diversity. The diagnostic test will also make it possible to investigate if the IGF2*Q mutation is associated with any unfavorable effects on meat quality or any other trait. We and others have previously demonstrated that European and Asian pigs were domesticated from different subspecies of the Wild Boar, and that Asian germplasm has been introgressed into European pig breeds.[17] The IGF2*Q mutation apparently occurred on an Asian chromosome as it showed a very close relationship to the haplotype carried by Chinese Meishan pigs. This explains the large genetic distance that we observed between Q- and q-haplotypes (FIG. 4). However, it is an open question whether the Q mutation occurred before or after the Asian chromosome was introduced into European pigs.

This study provides new insights in IGF2 biology. The role of IGF2 on prenatal development is well documented.[18, 19] Our observation that the Q mutation does not up-regulate IGF2 expression in fetal tissue until after birth, which demonstrates that IGF2 has an important role for regulating postnatal myogenesis. The finding that the sequence around the mutation does not match any known DNA-binding site suggests that this sequence may bind an unknown nuclear factor.[14] Our results also mean that pharmacological intervention of the interaction between this DNA segment and the corresponding nuclear factor opens up new strategies for promoting muscle growth in human patients with muscle deficiencies or for stimulating muscle development at the cost of adipose tissue in obese patients.

Materials and Methods

DNA Sequencing

Animals that were homozygous for 13 of the haplotypes of interest were identified using flanking microsatellite markers and pedigree information. A 28.6 kb chromosome segment containing the last exon of TH, INS, and IGF2 was amplified from genomic DNA in seven long-range PCR products using the Expand Long Template PCR system (Roche Diagnostics GmbH). The same procedure was used to amplify the remaining M220 and LW197 haplotypes from two BAC clones isolated from a genomic library that was made from a Meishan/Large White $F_1$ individual.[20] The long template PCR products were subsequently purified using Geneclean (Polylab) and sequenced using the Big Dye Terminator Sequencing or dGTP Big Dye Terminator kits (Perkin Elmer). The primers used for PCR amplification and sequencing are available as supplementary information. The sequence traces were assembled and analyzed for DNA sequence polymorphism using the Polyphred/Phrap/Consed suite of programs.[21]

SNP Analysis of IGF2-Intron3-Nt3072

The genotype was determined by pyrosequencing with a Luc 96 instrument (Pyrosequencing AB). A 231 bp DNA fragment was PCR amplified using Hot Star Taq DNA polymerase and Q-Solution (QIAGEN) with the primers pyro18274F (5'-Biotine-GGGCCGCGGCTTCGCCTAG-3') (SEQ ID NO:2) and pyro18274R (5'-CGCACGCTTCTCCT-GCCACTG-3') (SEQ ID NO:3) The sequencing primer (pyro18274seq: 5'-CCCCACGCGCTCCCGCGCT-3') (SEQ ID NO:4) was designed on the reverse strand because of a palindrome located 5' to the QTN.

Electrophoretic Mobility Shift Analyses (EMSA)

DNA-binding proteins were extracted from C2C12, HEK293, and HepG2 cells as described.[22] Gel shift assays were performed with 40 fmole $^{32}$P-labeled ds-oligonucleotide, 10 µg nuclear extract, and 2 µg poly dI-dC in binding buffer (15 mM Hepes pH 7.65, 30.1 mM KCl, 2 mM $MgCl_2$, 2 mM spermidine, 0.1 mM EDTA, 0.63 mM DTT, 0.06% NP-40, 7.5% glycerol). For competition assays, a ten-fold, 20-fold, 50-fold, and 100-fold molar excess of cold ds-oligonucleotide were added. Reactions were incubated for 20 minutes on ice before $^{32}$P-labeled ds-oligonucleotide was added. Binding was then allowed to proceed for 30 minutes at room temperature. DNA-protein complexes were resolved on a 5% native polyacrylamide gel run in TBE 0.5× at room temperature for two hours at 150 V and visualized by autoradiography. The following two oligonucleotides were used: Q/q: 5'-GATCCTTCGCCTAGGCTC(A/G)CAGCGCGG-GAGCGA-3' (SEQ ID NO: 1).

Northern Blot Analysis and Real-Time RT-PCR

Total RNA was prepared from porcine muscle (gluteus) and liver tissues using Trizol (Invitrogen) and treated with DNase I (Ambion). The products from the first-strand cDNA synthesis (Amersham Biosciences) were column purified with QIAQUICK® columns (Qiagen). Poly (A)$^+$ RNA was purified from total RNA using the Oligotex mRNA kit (Qiagen). Approximately 75 ng poly(A)$^+$ mRNA from each sample was separated by electrophoresis in a MOPS/formaldehyde agarose gel and transferred onto a Hybond-N+ nylon membrane (Amersham Biosciences). The membrane was hybridized with pig-specific IGF2 and GAPDH cDNA probes using ExpressHyb hybridization solution (Clontech). The quantification of the transcripts was performed with a Phosphor Imager 425 (Molecular Dynamics). Real-time PCR were performed with an ABI PRISM 7700 Sequence Detection System (Applied Biosystems). TaqMan probes and primers were designed with the Primer Express software (version 1.5); primer and probe sequences are available as supplementary material. PCR reactions were performed in triplicate using the Universal PCR Master Mix (Applied Biosystems). The mRNA was quantified as copy number using a standard curve. For each amplicon, a ten point calibration curve was established by a dilution series of the cloned PCR product.

Bisulphite-Based Methylation Analysis

Bisulphite sequencing was performed according to Engemann et al.[23] Briefly, high molecular weight genomic DNA was isolated from tissue samples using standard procedures based on proteinase K digestion, phenol-chloroform extraction, and ethanol precipitation. The DNA was digested with EcoRI, denatured, and embedded in low melting point agarose beads. Non-methylated cytosine residues were converted to uracil using a standard bisulphite reaction. The region of interest was amplified using a two-step PCR reaction with primers complementary to the bisulphite converted DNA sequence (PCR1-UP: 5'-TTGAGTGGGGATTGT-TGAAGTTTT-3' (SEQ ID NO:7), PCR1-DN: 5'-ACCCACT-TATAATCTAAAAAAATAATAAATATATCTAA-3' (SEQ ID NO:8), PCR2-UP: 5'-GGGGATTGTTGAAGTTTT-3' (SEQ ID NO:9), and PCR2-DN: 5'-CTTCTCCTACCAC-TAAAAA-3') (SEQ ID NO:10). The amplified strand was chosen in order to be able to differentiate the Q and q alleles. The resulting PCR products were cloned in the pCR2.1 vector (Invitrogen). Plasmid DNA was purified using the modified Plasmid Mini Kit (QIAGEN) and sequenced using the Big Dye Terminator Kit (Perkin Elmer) and an ABI3100 sequence analyzer.

Transient Transfection Assay

C2C12 myoblast cells were plated in six-well plates and grown to ~80% confluence. Cells were transiently co-transfected with a Firefly luciferase reporter construct (4 µg) and a Renilla luciferase control vector (phRG-TK, Promega; 80 ng) using 10 µg Lipofectamine 2000 (Invitrogen). The cells were incubated for 24 hours before lysis in 100 µl Triton Lysis Solution. Luciferase activities were measured with a Mediators PhL luminometer (Diagnostic Systems) using the Dual-Luciferase reporter Assay System (Promega).

Analysis of the IGF2 Imprinting Status

RT-PCR analysis of the highly polymorphic SWC9 microsatellite (located in IGF2 3'UTR) was used to determine the IGF2 imprinting status. The analysis involved progeny groups from heterozygous sires. Total RNA was extracted from the gluteus muscle using Trizol Reagent (Life Technology), and treated with RNase-free DNase I (Roche Diagnostics GmbH). cDNA was synthesized using the $1^{st}$ Strand cDNA Synthesis Kit (Roche Diagnostics GmbH). The SWC9 marker was amplified using the primers UP (5'-AAGCAC-CTGTACCCACACG-3') (SEQ ID NO: 11) and DN (5'-GGCTCAGGGATCCCACAG-3') (SEQ ID NO: 12). The $^{32}$P-labeled RT-PCR products were separated by denaturing PAGE and revealed by autoradiography.

Example 3

The Mutation has an Effect on Teat Number

Sires of two commercial lines were genotyped for the mutation. Shortly after birth, the number of teats was counted on all piglets. Piglet counts ranged from 12 to 18 teats and included 4477 individuals from 22 sires. A statistical analysis of teat number in piglets was performed by accounting for the following effects: 1) genetic line (lines A and B), 2) genotype of the sire for the mutation (QQ, Qq or qq) and 3) sex of the piglet (male/female). Analysis of variance was performed using Proc Mixed (SAS) assuming normality of dependent variable teat number. Estimates of some contrasts are given in Table 4.

The effect of genotype on teat number in piglets is −0.28 teats. This effect is opposite to the one described by Hirooka et al. 2001. An effect of genetic line could not be demonstrated. The sex of the piglet had a significant effect on teat number with female pigs having an average of 0.05 teat more than males. Mean values per genotype and per line are given in Table 5.

The statistical analysis confirms that the mutation influences teat number. The Q allele that is favorable with respect to muscle mass and reduced back fat is the unfavorable allele for teat number. This strengthens the possibility of using the paternal imprinting character of this QTL in breeding programs. Selecting maternal lines for the q allele will enhance teat number, a characteristic that is favorable for the maternal side. On the other hand, paternal lines can be selected for the Q allele that will increase muscle mass and reduce back fat, characteristics that are of more importance in the paternal lines. Terminal sires that are homozygous QQ will pass the full effect of increased muscle mass and reduced back fat to the slaughter pigs, while selection of parental sows that express the q allele will have more teats without affecting slaughter quality.

Example 4

The Mutation has an Effect on Sow Longevity and Sow Prolificacy

This example shows the presently described unique inheritance method of paternal imprinting, wherein only the gene inherited from the father is expressed, and wherein the gene inherited from the mother is a silent gene and has no effect on the carcass quality of the offspring.

Materials and Methods

Animals. The animals used in this experiment are purebred animals belonging to three different closed dam lines based on Large White and Landrace breeds. From 1999 until 2005, blood samples were collected from all nucleus sows and boars. Genotypic frequencies per line were calculated on 555 sows in total.

Measurements. Individual blood samples are linked to individual phenotypes. For all sows, the following parameters were recorded: total born, live born, stillborn and weaned piglets per litter. At test weight of 110 kg, carcass measures were performed on live animals using Piglog 105 (including back fat 1, back fat 2 (3rd-4th rib), loin eye depth and lean meat percentage).

Genotyping. DNA was extracted from the pig blood samples using the Wizard Genomic DNA purification kit according to procedures provided by the manufacturer (Promega, Madison Wis., USA). An allelic discrimination assay was performed using the ABI Prism 7700 sequence detection system (Applied Biosystems). The final concentrations used in the 5 µl master mix were: 2.5 µl Taqman Universal PCR Master Mix, NoAmpErase Ung (Applied Biosystems, Foster City, Calif., USA), 1× Assay Mix, 10 ng DNA and 2,375 µl $H_2O$, Foster City, USA).

Statistical analyses. The statistical analysis was performed using the statistical software SAS. The gene frequencies were calculated from PROC FREQ. IGF2 effects were analyzed using SAS PROC GLM with paternal or maternal allele as class variables and taking into account parity and sire. For the calculation of the effect of the IGF2 mutation on the traits measured, a subset of data was made in which only sows that originate from sires that are heterozygous for the IGF2 mutation were used. Sows that inherited the G allele were compared with those that inherited the A allele. Another subset of data was made in which only sows from heterozygous dams were retained. In this dataset, the effect of the maternal allele was analyzed.

Results and Discussion. Allelic frequencies are presented in Table 6. All three dam lines segregate for the IGF2 mutation, although frequencies differ according to the line.

A subset of data was made in which only sows derived from heterozygous sires that segregate in the population were retained. A comparison was made between sows that inherited the A or the G allele from their father.

Sows that inherited the wild-type allele from their father had significantly more piglets born alive, total born and weaned, while there was no effect on stillborn piglets (Table 7). If the same dataset was analyzed, according to the allele inherited from the mother (maternal allele), no effect on any of these prolificacy data could be observed. A second subset of data was created in which only sows from heterozygous dams were taken into account and grouped according to the maternal allele. Again, no significant effect on prolificacy could be observed, which was expected since the maternal allele is not expressed.

The parity or average number of cycles per sow was also higher in sows that inherited G from their father as compared to those that received the A allele, which points to a beneficial effect on longevity. This is related to higher litter size, since that is a major criterion for elimination in the selection program.

The effect of the paternal allele for IGF2 was also analyzed on conformation measures at ca. 110 kg live weight. These data are presented in Table 8.

Although no significant effects of IGF2 paternal allele on Piglog results could be observed, there is a tendency towards higher muscularity and lower back fat in the sows that inherited the A allele from their father. The fact that this difference is not significant could be due to the low number of animals on the one hand and the use of a threshold value on back fat in the selection program on the other.

These results show an influence of the IGF2-intron3 G3072A mutation on prolificacy and longevity in sows. This opens the possibilities to use the same imprinted QTN for different selection in sire and dam lines. Terminal sires should be homozygous for the lean allele to give uniform and lean slaughter pigs, while dam lines can benefit from a selection for the wild-type allele since this has a beneficial effect on prolificacy and longevity. Because of the imprinted character of the gene, selection for the fatter allele in sow lines will not influence the carcass quality of the offspring.

A suitable marker-assisted selection program for the IGF2 mutation may now be represented as depicted in FIG. 1.

TABLE 1

Utilized sequence tagged sites (STS) and corresponding DNA sequence polymorphisms (DSP).

| STS | Source | UP-primer (5'-3') | DN-primer (5'-3') | DSP[2] | DSP (5'-3') |
|---|---|---|---|---|---|
| TSSC5(I1)[1] | BI183986 | TCATCCAGGGCCTGGTCATCG (SEQ ID NO: 13) | TGTCTGAGGCCGACACGGCC (SEQ ID NO: 14) | T1 | CCCCCT(C/T)GGCCCCC (SEQ ID NO: 15) |
| | | | | T2 | ACCCAGGGC(C/T)CCTTGAG (SEQ ID NO: 16) |
| SWR2516 | gi7643973 | GTGCATTATCGGGAGGTATG (SEQ ID NO: 17) | ACCCTGTATGATACTGTAACTCTGG (SEQ ID NO: 18) | SSR | ATAGGGTTA(GT)nAGATCAGTC (SEQ ID NO: 19) |
| KVLQT1(SSR) | BAC956B11 | CTTTGAGGTCCATCATGTTCCA (SEQ ID NO: 20) | GGACGTACATCCCATCGATGA (SEQ ID NO: 21) | SSR | |
| KVLQT1(I12) | BF198846 | ATGGTTGTCCTCTGCGTGGGC (SEQ ID NO: 22) | TGGCGGTCGACGTGCAGCATC (SEQ ID NO: 23) | T1 | TGGGTGGGG(C/T)GCAGCCCC (SEQ ID NO: 24) |
| | | | | T2 | GCTGGGA(C/T)CAGACC(G/A)TCTGGG (SEQ ID NO: 25) |
| | | | | T3 | GCTGGGA(C/T)CAGACC(G/A)TCTGGG (SEQ ID NO: 25) |
| | | | | T4 | CTGTCTGCTCAT(C/T)CGGGGGCTG (SEQ ID NO: 26) |
| | | | | T5 | GGCTGCGGGAGC(C/T)TGGGGCCAC (SEQ ID NO: 27) |
| | | | | T6 | GCCACCCCC(C/T)TGACCCTGA (SEQ ID NO: 28) |
| KVLQT1(I11) | BF198846 | ATCCGCTTCCTCCAGATCCTG (SEQ ID NO: 29) | GCCGATGTACAGCGTGGTGA (SEQ ID NO: 30) | V1 | TCTGGGCCGG(G/T)GTCCCCG (SEQ ID NO: 31) |
| | | | | T1 | AAAAGGGTCC(A/G)GGAAGCT (SEQ ID NO: 32) |
| | | | | T2 | TTGCAAACAGC(C/T)CCCAGAAGG (SEQ ID NO: 33) |
| | | | | T3 | AGAAGGCGCAG(C/T)CTCCACGGG (SEQ ID NO: 34) |
| | | | | T4 | AGGGGCGCTGG(C/T)TGCAGGGGTG (SEQ ID NO: 35) |
| | | | | T5 | TTTATGAGTC(A/G)CAAAAACGAG (SEQ ID NO: 36) |
| | | | | T6 | TGATGTCCGCC(C/T)(G/T)GGCAGACT (SEQ ID NO: 37) |
| | | | | V2 | TGATGTCCGCC(C/T)(G/T)GGCAGACT (SEQ ID NO: 37) |
| KVLQT1(I7) | BF198846 | GCCCCAAGCCCAAGAAGTCTG (SEQ ID NO: 38) | CCAGAATTGTCACAGCCATCC (SEQ ID NO: 39) | T | TCCGGGGCAT(A/G)TAGGACTGG (SEQ ID NO: 40) |

TABLE 1-continued

Utilized sequence tagged sites (STS) and corresponding DNA sequence polymorphisms (DSP).

| STS | Source | UP-primer (5'-3') | DN-primer (5'-3') | DSP[2] | DSP (5'-3') |
|---|---|---|---|---|---|
| 389B2T7 | BAC389B2 | GGAGTACCTGCTGTGGCTT AGTG (SEQ ID NO: 41) | CGTCCTATATCCATCAGGAATA TTG (SEQ ID NO: 42) | T1 | AGTAGTAT(C/T)CATGAGCAC (SEQ ID NO: 43) |
| | | | | T2 | CCCAGGCCTC(G/A)ATCAGCTGGTTG (SEQ ID NO: 44) |
| | | | | V | TATATGCCA(C/A)ACATGTGGCCCT (SEQ ID NO: 45) |
| CD81(I3) | F23061 | GGGGCCATCCAGGAGTCAC AG (SEQ ID NO: 46) | CAAAGAGGATCACGAGGCAGG (SEQ ID NO: 47) | | |
| INRA370SP6 | BACINRA370 | TGCGTAGCCATGGCGATGG GG (SEQ ID NO: 48) | AGTGTGGAACCCTGGGGGGGA AGG (SEQ ID NO: 49) | | |
| 370C17T7 | BAC370C17 | AGAGGGTACAGAAGCCCTG (SEQ ID NO: 50) | TTTGGTGTGGTGTCTGCTGAC CC (SEQ ID NO: 51) | | |
| PULGE3 | BACINRA370 | AGGCTTTCTATCTGCAGGA GG (SEQ ID NO: 52) | ACCGTGTGGCCATCTGGGTG (SEQ ID NO: 53) | SSR | TCTCTGTAT(CA)nCGCACGCAC (SEQ ID NO: 54) |
| PULGE1 | BACINRA370 | GCGTTGCAGTGGCTCTGG CG (SEQ ID NO: 55) | GACACGGCCGCATGAATGTGC (SEQ ID NO: 56) | SSR | ACCCCAACA(TA)nATTATGGTA (SEQ ID NO: 57) |
| TH(I13A) | AY044828 | GCCCGTCTACTTCGTGTCT GAG (SEQ ID NO: 58) | ATCTCTGCCTTCATCGCACCC CC (SEQ ID NO: 59) | V | AGGATCCAGCC(A/T)GCAGCCCCG (SEQ ID NO: 60) |
| | | | | ID | TCACAACCCCC(C)TCCCACAGC (SEQ ID NOS: 61 and 62) |
| | | | | T | CTGCGGAGGGG(A/G)GACCTGCAG (SEQ ID NO: 63) |
| TH(I13B) | AY044828 | GCTGCGGACCCCACCGTC AC (SEQ ID NO: 64) | AGACTTCACCCCTAAAAGCCT GG (SEQ ID NO: 65) | ID | GCCAGGT(CAAGGCCAGGT)CGAGGCC (SEQ ID NOS: 66 and 67) |
| INS(5') | AY044828 | AGCAGGCTGCTGTGCTGGG (SEQ ID NO: 68) | AGCCCAGACCCAGCTGACGG (SEQ ID NO: 69) | T1 | GGCGCTTATGG(G/A)GCCGGGAGC (SEQ ID NO: 70) |
| | | | | V | CAAGCCCGG(G/T)CGGTTTGGCCT (SEQ ID NO: 71) |
| | | | | T2 | CTAATGACCTC(A/G)AGGCCCCCA (SEQ ID NO: 72) |
| INS(I1, E2, I2) | AY044828 | TGATGACCCACGGAGATGA TCC (SEQ ID NO: 73) | GCAGTAGTTCTCCAGCTGGTAG AGGGAA (SEQ ID NO: 74) | T1 | GGGACCAGCTG(C/T)GTTCCCAGG (SEQ ID NO: 75) |
| | | | | V | GCCCTGCTGGC(C/G)CTCTGGGCG (SEQ ID NO: 76) |
| | | | | T2 | CTCCCACGCCC(C/T)GGTCCCGCT (SEQ ID NO: 77) |
| INS(3') | AY044828 | GCTCTCGGCCACATCGGCT GC (SEQ ID NO: 78) | GGCGCCCAGCTCTAGGCCCGGC (SEQ ID NO: 79) | T | GGGCTGGCTGC(G/A)GTCTGGGAG (SEQ ID NO: 80) |
| IGF2(E3) | AY044828 | CCCCTGAACTTGAGGACGA GCAGCC (SEQ ID NO: 81) | CGCTGTGGGCTGGGTGGGCTG CC (SEQ ID NO: 82) | T | GCTGCCCCCCA(A/G)CCTGAGCTG (SEQ ID NO: 83) |
| IGF2(E5) | AY044828 | CTTGCCTCCAACTCCCTC CC (SEQ ID NO: 84) | AGTGAACGTGAAACGGGGGG (SEQ ID NO: 85) | SSR | CTCTCGCTGTC(CT)nCGCCCTCTCTT (SEQ ID NO: 86) |
| IGF2(I8) | AY044828 | TGCGCCACCCCCGCCAAGT CC (SEQ ID NO: 87) | GCTTCCAGGTGTCATAGCGGA AG (SEQ ID NO: 88) | V | AGCCGGCTCCT(G/C)GGCTTCAAG (SEQ ID NO: 89) |
| | | | | T | AGAGGTTGTTC(C/T)TCTGGGACA (SEQ ID NO: 90) |
| SWC9 | AY044828 | AAGCACCTGTACCCACACG (SEQ ID NO: 91) | GGCTCAGGGATCCCACAG (SEQ ID NO: 92) | SSR | (CA)n |
| IG(IGF2-H19) | AY044828 | CACCGCCAGGTCCTGTCGA GG (SEQ ID NO: 93) | GGACCCTGGGGGCTGTGG (SEQ ID NO: 94) | T | CGGCCTGTGGC(A/G)GGGAAGCTG (SEQ ID NO: 95) |

TABLE 1-continued

Utilized sequence tagged sites (STS) and corresponding DNA sequence polymorphisms (DSP).

| STS | Source | UP-primer (5'-3') | DN-primer (5'-3') | DSP[2] | DSP (5'-3') |
|---|---|---|---|---|---|
| H19(??) | AY044828 | ACGGTCCCGGGTCAGCAGG (SEQ ID NO: 96) | CAGAGCAAGTGGGCACCCAG (SEQ ID NO: 97) | T1 | CGCGGGTTTGG(C/T)CAGCGGCAG (SEQ ID NO: 98) |
| | | | | T2 | CACAGAGGACA(C/T)GGCCGCTTC (SEQ ID NO: 99) |
| | | | | T3 | TCCTGGGGGCC(C/T)GCGGCTCGT (SEQ ID NO: 100) |
| IG(H19-RL23mrp)A | AY044828 | GAGCACAGCCAAAGAACGGCCG (SEQ ID NO: 101) | CTTCACCCACGGACATGGCCGC (SEQ ID NO: 102) | T | CACCCAGGCTG(C/T)GCCCTGCGT (SEQ ID NO: 103) |
| IG(H19-RL23mrp)B | AY044828 | CGGGGGCACTGGGGGTCC (SEQ ID NO: 104) | CCGAGACCCTCCTCAAGTCC (SEQ ID NO: 105) | T | GTTCGCCCTCC(A/G)CTCTCAGCA (SEQ ID NO: 106) |
| IG(H19-RL23mrp)C | AY044828 | TGAGCTGCTGAGCCCACAGG (SEQ ID NO: 107) | CAAGGGAAAGGTGTGCCGACC (SEQ ID NO: 108) | T | GGCCGGGCGCT(C/T)CGCCTTCCC (SEQ ID NO: 109) |
| IG(H19-RL23mrp)D | AY044828 | AGGCAGAGGGCAGAGAGGGG (SEQ ID NO: 110) | CTCCAGCCCCACACTCTGC (SEQ ID NO: 111) | T | GCGTCCAGCGC(C/T)GAATCAGGC (SEQ ID NO: 112) |

[1] I = intron; E = exon.
[2] DSP: type of DNA sequence polymorphism: T = transition, V = transversion, ID = insertion/deletion, SSR = simple sequence repeat.

TABLE 2

Definition of the multisite haplotypes corresponding to the different markers shown in FIGS. 2 and 3.

| STS | MH1 | MH2 | MH3 | MH4 | MH5 |
|---|---|---|---|---|---|
| TSSC5(I1) | T-T | C-C | | | |
| KVLQT1(I12) | C-C-C-G-C-C | C-T-T-A-T-C | C-C-A-T-T | | |
| KVLQT1(I11) | T-C-G-C-T-T-G-T | G-T-A-T-C-C-A-T | G-C-G-C-C-C-G-G | | |
| 389B2T7 | C-G-C | T-A-A | | | |
| TH1 + TH2 | T-C-G-(CAAGGCCAGGT) (SEQ ID NO: 113) | A-(-)-A-(-) | A-C-G-(CAAGGCCAGGT) (SEQ ID NO: 114) | | |
| INS(5') + IN2(I1, E2, I2) + INS(3') | G-G-A-C-C-C-G | A-T-G-T-G-T-A | G-G-G-T-G-C-G | | |
| IGF2(E3) + IGF2(E5) + IGF2(I8) | G-2-G-T | A-2-C-C | A-1-G-T | A-2-G-T | G-2-G-T |
| H19 | C-C-T | C-C-C | C-T-C | T-T-C | |
| IG(H19-RL23MRP)A, B, C, D | C-A-T-T | T-G-C-C | | | |

TABLE 3

Distribution of genotypes at the Quantitative Trait Nucleotide IGF2-intron3-nt3072G→A among pig populations strongly selected (+) or not strongly selected (−) for lean growth.

| Breed | Lean | G/G | G/A | A/A | Total |
|---|---|---|---|---|---|
| European Wild Boar | − | 5 | 0 | 0 | 5 |
| European Wild Boar - Uppsala[a] | − | 2 | 0 | 0 | 2 |
| Japanese Wild Boar | − | 5 | 0 | 0 | 5 |
| Meishan - Roslin[b] | − | 11 | 0 | 0 | 11 |
| Large White - Uppsala[a] | + | 0 | 1 | 7 | 8 |
| Large White - Roslin[b] | + | 6 | 1 | 0 | 7 |
| Large White - Liège[c] | + | 7 | 0 | 0 | 7 |
| Swedish Large White[d] | + | 0 | 0 | 5 | 5 |
| Swedish Hampshire[d] | + | 0 | 0 | 6 | 6 |
| Swedish Landrace[d] | + | 0 | 0 | 5 | 5 |
| Piétrain - Liège[c] | + | 0 | 1 | 6 | 7 |
| Duroc | + | 0 | 0 | 1 | 1 |
| Total | | 45 | 3 | 30 | 78 |

[a]Founder animals in a Wild Boar × Large White intercross (2).
[b]Founder animals in a Large White × Meishan intercross (16).
[c]Founder animals in a Piétrain × Large White intercross (1).
[d]Breeding boars that have been tested for QTL segregation in a previous study (8). The lack of evidence for QTL segregation shows that they can all be considered homozygous at the IGF2 locus.

TABLE 4

Analysis of variance of teat number counted in piglets of two commercial lines (n = 4477).

| Effect | P-value | Contrast | Estimate(s.e) |
|---|---|---|---|
| Genotype of sire | <0.001 | QQ-qq | −0.28 (0.05) |
| Genetic line | 0.081 | Qq-qq | −0.22 (0.03) |
| Sex | 0.043 | M-F | −0.05 (0.03) |

TABLE 5

Descriptive statistics of teat number counted in piglets of two commercial lines (n = 4477) descending from sires of 3 different genotypes with respect to the mutation.

| | Genotype | N sires | N descending piglets | Average teat number | Stdev |
|---|---|---|---|---|---|
| A | QQ | 2 | 144 | 14.51 | 0.76 |
|   | Qq | 5 | 1720 | 14.53 | 0.82 |
|   | qq | 3 | 735 | 14.74 | 0.86 |
| B | QQ | 2 | 277 | 14.41 | 1.00 |
|   | Qq | 7 | 1054 | 14.48 | 0.81 |
|   | qq | 3 | 547 | 14.73 | 0.93 |

TABLE 6

Allele frequencies for the IGF2-intron3 G3072A mutation in sows of dam lines (Number of sows within genotypes is presented in parenthesis)

| Line | AA | GA | GG |
|---|---|---|---|
| A | 0.04 (4) | 0.28 (25) | 0.68 (61) |
| B | 0.30 (42) | 0.37 (52) | 0.33 (46) |
| C | 0.80 (259) | 0.19 (62) | 0.01 (4) |

TABLE 7

Effect of paternal allele inherited from heterozygous sires on prolificacy

| Trait | A | G | Significance* |
|---|---|---|---|
| Number of cycles analyzed* | 240 | 276 | |
| Born alive/litter | 10.37 ± 0.18 | 10.90 ± 0.16 | 0.0075 |
| Total born/litter | 11.04 ± 0.19 | 11.48 ± 0.17 | 0.0371 |
| Stillborn/litter | 0.63 ± 0.07 | 0.59 ± 0.06 | NS |
| Weaned/litter | 9.11 ± 0.21 | 9.92 ± 0.16 | 0.0134 |
| Parity | 2.95 ± 0.12 | 3.54 ± 0.12 | 0.0035 |

*Model taking parity and sire into account,
NS = not significant P > 0.05

TABLE 8

Effect of paternal allele inherited from heterozygous sires on carcass measures at 110 kg live weight (Piglog 105)

| Trait | A | G | Significance* |
|---|---|---|---|
| Number of sows analyzed* | 70 | 64 | |
| Back fat 1 (mm) | 14.90 ± 0.27 | 15.08 ± 0.27 | NS |
| Back fat 2 (mm) | 13.20 ± 0.29 | 14.14 ± 0.30 | NS |
| Loin eye (mm) | 56.28 ± 0.45 | 55.72 ± 0.41 | NS |
| % lean meat | 57.31 ± 0.26 | 56.69 ± 0.28 | NS |

*Model taking sire into account.
NS = not significant P > 0.05

REFERENCES OF EXAMPLE 1

Amarger V., M. Nguyen, A. S. Van Laere, C. Nezer, M. Georges, and L. Andersson (2002). Comparative sequence analysis of the INS-IGF2-H19 gene cluster in pigs. *Mammalian Genome* 13:388-398.

Andersson L. (2001). Genetic dissection of phenotypic diversity in farm animals. *Nature Reviews Genetics* 2:130-138.

Ardlie K. G., L. Kruglyak, and M. Seielstad (2002). Patterns of linkage disequilibrium in the human genome. *Nat. Rev. Genet.* 3:299-309.

Blott S., J.-J. Kim, S. Moisio, A. Schmidt-Küntzel, A. Cornet, P. Berzi, N. Cambisano, C. Ford, B. Grisart, D. Johnson, L. Karim, P. Simon, R. Snell, R. Spelman, J. Wong, J. Vilkki, M. Georges, F. Farnir, and W. Coppieters (2002). Molecular dissection of a QTL: a phenylalanine to tyrosine substitution in the transmembrane domain of the bovine growth hormone receptor is associated with a major effect on milk yield and composition. *Genetics*, in the press.

Darvasi A. (1998). Experimental strategies for the genetic dissection of complex traits in animal models. *Nat. Genet.* 18:19-24.

Dunner S., C. Charlier, F. Farnir, B. Brouwers, J. Canon, and M. Georges (1997). Towards interbreed IBD fine mapping of the mh locus: double-muscling in the Asturiana de los Valles breed involves the same locus as in the Belgian Blue cattle breed. *Mammalian Genome* 8:430-435.

Fahrenkrug S. C., G. A. Rohrer, B. A. Freking, T. P. Smith, K. Osoegawa, C. L. Shu, J. J. Catanese, and P. J. de Jong (2001). A porcine BAC library with ten-fold genome coverage: a resource for physical and genetic map integration. *Mamm. Genome* 12:472-474.

Flint J. and R. Mott (2001). Finding the molecular basis of quantitative traits: successes and pitfalls. *Nature Reviews Genetics* 2:437-445.

Florini J. R., D. Z. Ewton, and S. A. Coolican (1996). Growth hormone and the insulin-like growth factor system in myogenesis. *Endocr. Rev.* 17:481-517.

Georges M., D. Nielsen, M. Mackinnon, A. Mishra, R. Okimoto, A. T. Pasquino, L. S. Sargeant, A. Sorensen, M. R. Steele, X. Zhao, J. E. Womack and I. Hoeschele (1995). Mapping quantitative trait loci controlling milk production by exploiting progeny testing. *Genetics* 139:907-920.

Grisart B., W. Coppieters, F. Farnir, L. Karim, C. Ford, N. Cambisano, M. Mni, S. Reid, R. Spelman, M. Georges and R. Snell (2002). Positional candidate cloning of a QTL in dairy cattle: Identification of a missense mutation in the bovine DGAT gene with major effect on milk yield and composition. *Genome Research* 12:222-231.

Grobet L., L. J. Royo Martin, D. Poncelet, D. Pirottin, B. Brouwers, J. Riquet, A. Schoeberlein, S. Dunner, F. Menissier, J. Massabanda, R. Fries, R. Hanset, and M. Georges (1997). A deletion in the myostatin gene causes double-muscling in cattle. *Nature Genetics* 17:71-74.

Hanset R., C. Dasnois, S. Scalais, C. Michaux, and L. Grobet (1995). Effets de l'introgression dans le genome Piétrain de l'allèle normal au locus de sensibilité à l'halothane. *Genet. Sel. Evol.* 27:77-88.

Hirooka H., D. J. De Koning, B. Harlizius, J. A. M. Van Arendonk, A. P. Rattink, M. A. M. Groenen, P. Brascamp, and H. Bovenhuis (2001). A whole-genome scan for quantitative trait loci affecting teat number in pigs. *J. Anim. Sci.* 79:2320-2326.

Jeon J. T., O. Carlborg, A. Törnsten, E. Giuffra, V. Amarger, P. Chardon, L. Andersson-Eklund, K. Andersson, I. Hansson, K. Lundström, and L. Andersson (1999). A paternally expressed QTL affecting skeletal and cardiac muscle mass in pigs maps to the IGF2 locus. *Nat. Genet.* 21:157-158.

MacKay T. F. C. (2001). Quantitative Trait Loci in Drosophila. *Nature Reviews Genetics* 2:11-20.

Mauricio R. (2001). Mapping quantitative trait loci in plants: uses and caveats for evolutionary biology. *Nature Reviews Genetics* 2:370-381.

Meuwissen T. H. and M. E. Goddard (2001). Prediction of identity by descent probabilities from marker-haplotypes. *Genet. Sel. Evol.* 33:605-634.

Milan D., J. T. Jeon, C. Looft, V. Amarger, A. Robic, M. Thelander, C. Rogel-Gaillard, S. Paul, N. Iannuccelli, L. Rask, H. Ronne, K. Lundstrom, N. Reinsch, J. Gellin, E. Kalm, P. L. Roy, P. Chardon, and L. Andersson (2000). A mutation in PRKAG3 associated with excess glycogen content in pig skeletal muscle. *Science* 288:1248-1251.

Nezer C., L. Moreau, B. Brouwers, W. Coppieters, J. Detilleux, R. Hanset, L. Karim, A. Kvasz, P. Leroy, and M. Georges (1999). An imprinted QTL with major effect on muscle mass and fat deposition maps to the IGF2 locus in pigs. *Nat. Genet.* 21:155-156.

Nezer C., L. Moreau, D. Wagenaar, and M. Georges (2002). Results of a whole genome scan targeting QTL for growth and carcass characteristics in a Piétrain X Large White intercross. Genetics, Selection, Evolution 34:371-387.

Onyango P., W. Miller, J. Lehoczky, C. T. Leung, B. Birren, S. Wheelan, K. Dewar, and A. P. Feinberg (2000). Sequence and Comparative Analysis of the Mouse 1-Megabase Region Orthologous to the Human 11p15 Imprinted Domain. *Genome Res.* 10: 1697-1710.

Reid W. and J. Walter (2001). Genomic imprinting: parental influence on the genome. *Nature Reviews Genetics* 2:21-32.

Riquet J., W. Coppieters, N. Cambisano, J.-J. Arranz, P. Berzi, S. Davis, B. Grisart, F. Farnir, L. Karim, M. Mni, P. Simon, J. Taylor, P. Vanmanshoven, D. Wagenaar, J. E. Womack, and M. Georges (1999). Identity-by-descent fine-mapping of QTL in outbred populations: application to milk production in dairy cattle. *Proceedings of the National Academy of Sciences, US* 96:9252-9257.

Sabeti P. C., D. E. Reich, J. M. Higgins, H. Z. Levine, D. J. Richter, S. F. Schaffner, S. B. Gabriel, J. V. Platko, N. J. Patterson, G. J. McDonald, H. C. Ackerman, S. J. Campbell, D. Altshuler, R. Cooper, D. Kwiatkowski, R. Ward, and E. S. Lander (2002). Detecting recent positive selection in the human genome from haplotype structure. *Nature* 419:832-837.

Terwilliger J. D. (1995). A powerful likelihood method for the analysis of linkage disequilibrium between trait loci and one or more polymorphic marker loci. *Am. J. Hum. Genet.* 56:777-787.

REFERENCES AND NOTES OF EXAMPLE 2

1. Nezer C. et al., *Nature Genet.* 21:155-156 (1999).
2. Jeon J.-T. et al., *Nature Genet.* 21:157-158 (1999).
3. De Koning D. J. et al., *Proc. Natl. Acad. Sci. U.S.A.* 7947-7950 (2000).
4. Thomsen H., J. C. M. Dekkers, H. K. Lee, and M. Rothschild, paper presented at the 7th World Congress of Genetics Applied to Livestock Production, Montpellier, France 2002.
5. Nezer C. et al., submitted (2003).
6. Florini J. R., D. Z. Ewton, and F. J. Mcwade, *Diabetes Rev.* 3:73-92 (1995).
7. Amarger V. et al., *Mammalian Genome* 13:388-398 (2002).
8. Evans G. J. et al., *Genetics*, in press (2003).
9. QTL genotyping of the Pietrain/Large White, Wild Boar/Large White, and Hampshire/Landrace crosses by marker-assisted segregation analysis was performed as described.[5] Briefly, the likelihood of the pedigree data was computed under two hypothesis: H0, postulating that the corresponding boar was homozygous at the QTL (Q/Q or q/q), and H1 postulating that the boar was heterozygous at the QTL (Q/q). Likelihoods were computed using "% lean meat" as phenotype (as the effect of the QTL was shown to be most pronounced on this trait in previous analyses), and assuming a Q to q allele substitution effect of 3.0%.[1] If the odds in favor of one of the hypotheses were superior or equal to 100:1, the most likely hypothesis was considered to be true. For the Hampshire/Landrace cross, 75 offspring from four boars with identical H254/H205 genotype were merged in a single analysis. The odds in favor of the H0 hypothesis were 103.6:1, indicating that these boars were either Q/Q or q/q.
10. Mackay T. F. C., *Nature Rev. Genet.* 2:11-21 (2001).
11. Greally J. M., M. E. Guinness, J. Mcgrath, and S. Zemel, *Mammalian Genome* 8:805-810 (1997).
12. Constancia M. et al., *Nature Genet.* 26:203-206 (2000).
13. Eden S. et al., *EMBO J.* 20:3518-3525 (2001).
14. The nucleotide sequence of the conserved footprint surrounding the QTN was analyzed in silico for potential binding sites using the following transcription factor binding site databases (TFSEARCH, worldwideweb.cbrcjp/research/db/TFSEARCH.html; Tess, worldwideweb.cbil.upenn.edu/tess/; Signal Scan, worldwideweb.bimas.dcrt.nih.gov/molbio/signal/;[24] and alibaba2, worldwideweb.gene-regulation.de/). The sequence immediately flanking the QTN did not show any convincing match with known binding sites. However, the entire 94 bp fragment is highly GC-rich and, consequently, several potential binding sites for the Sp- (eight GC-boxes), ZF5 (one consensus binding site), EGR/WT1

(three GSG-elements), and AP2 (three AP-2-boxes) families of transcription factors were identified in sites flanking the QTN. Both activators and repressors are known to competitively or cooperatively interact with such GC-rich motifs. Thus, the high density of potential regulatory elements identified in this fragment is consistent with the obtained EMSA and transfection results.

15. Relative expression of IGF2/HPRT in skeletal muscle from three-week-old pigs was as follows: Q:260.2±70.8 and q:59.6±12.1 (P<0.05, Kruskal-Wallis rank sum test, two sided).
16. Walling G. A. et al., *Anim. Genet.* 29:415-424 (1998).
17. Giuffra E. et al., *Genetics* 154:1785-1791 (2000).
18. Dechiara T. M., A. Efstratiadis, and E. J. Robertson, *Nature* 345:78-80 (1990).
19. Sun F. L., W. L. Dean, G. Kelsey, N. D. Allen, and W. Reik, *Nature* 389:809-815 (1997).
20. Anderson S. I., N. L. Lopez-Corrales, B. Gorick, and A. L. Archibald, *Mammalian Genome* 11:811-814 (2000).
21. Nickerson D., V. O. Tobe, and S. L. Taylor, *Nucleic Acids Res.* 25:2745-2751 (1997).
22. Andrews N. C., and D. V. Faller, *Nucleic Acids Res.* 19:2499 (1991).
23. Engemann S., O. El-Maarri, P. Hajkova, J. Oswald, and J. Walter, in *Methods in Molecular Biology*, vol 181: Genomic imprinting: Methods and Protocols A. Ward, Ed. (Humana Press Inc., Totowa, N.J., 2002).
24. Prestridge D. S., *Comput. Appl. Biosci.* 7:203-206 (1991).
25. Kashuk C., S. Sengupta, E. Eichler, and A. Chakravarti, *Genome Res.* 12:333-338 (2002).
26. Kumar S., K. Tamura, I B. Jakobsen, and M. Nei, *Bioinformatics* 17:1244-1245 (2001).

SEQUENCE LISTING

```
<160> NUMBER OF SEQ ID NOS: 118

<210> SEQ ID NO 1
<211> LENGTH: 33
<212> TYPE: DNA
<213> ORGANISM: Artificial Sequence
<220> FEATURE:
<223> OTHER INFORMATION: Chemically synthesized - Stretch of nucleotides
      which in the wild type pig, mouse or human IGF2 gene is part of an
      evolutionary conserved CpG island
<220> FEATURE:
<221> NAME/KEY: misc_feature
<222> LOCATION: (19)..(19)
<223> OTHER INFORMATION: "n" stands for A or G

<400> SEQUENCE: 1
gatccttcgc ctaggctcnc agcgcgggag cga                                 33

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized - Primer pyro18274F

<400> SEQUENCE: 2
gggccgcggc ttcgcctag                                                 19

<210> SEQ ID NO 3
<211> LENGTH: 21
<212> TYPE: DNA
<213> ORGANISM: Artificial Sequence
<220> FEATURE:
<223> OTHER INFORMATION: Chemically synthesized - Primer pyro18274R

<400> SEQUENCE: 3
cgcacgcttc tcctgccact g                                              21

<210> SEQ ID NO 4
<211> LENGTH: 19
<212> TYPE: DNA
<213> ORGANISM: Artificial Sequence
<220> FEATURE:
<223> OTHER INFORMATION: Chemically synthesized - Primer pyro18274seq

<400> SEQUENCE: 4
ccccacgcgc tcccgcgct                                                 19
```

<210> SEQ ID NO 5
<211> LENGTH: 33
<212> TYPE: DNA
<213> ORGANISM: Artificial Sequence
<220> FEATURE:
<223> OTHER INFORMATION: Chemically synthesized - Oligonucleotide Q

<400> SEQUENCE: 5
gatccttcgc ctaggctcac agcgcgggag cga                          33

<210> SEQ ID NO 6
<211> LENGTH: 33
<212> TYPE: DNA
<213> ORGANISM: Artificial Sequence
<220> FEATURE:
<223> OTHER INFORMATION: Chemically synthesized - Oligonucleotide q

<400> SEQUENCE: 6
gatccttcgc ctaggctcgc agcgcgggag cga                          33

<210> SEQ ID NO 7
<211> LENGTH: 24
<212> TYPE: DNA
<213> ORGANISM: Artificial Sequence
<220> FEATURE:
<223> OTHER INFORMATION: Chemically synthesized - Primer PCR1-UP

<400> SEQUENCE: 7
ttgagtgggg attgttgaag tttt                                    24

<210> SEQ ID NO 8
<211> LENGTH: 38
<212> TYPE: DNA
<213> ORGANISM: Artificial Sequence
<220> FEATURE:
<223> OTHER INFORMATION: Chemically synthesized - Primer PCR1-DN

<400> SEQUENCE: 8
acccacttat aatctaaaaa aataataaat atatctaa                     38

<210> SEQ ID NO 9
<211> LENGTH: 18
<212> TYPE: DNA
<213> ORGANISM: Artificial Sequence
<220> FEATURE:
<223> OTHER INFORMATION: Chemically synthesized - Primer PCR2-UP

<400> SEQUENCE: 9
ggggattgtt gaagtttt                                           18

<210> SEQ ID NO 10
<211> LENGTH: 19
<212> TYPE: DNA
<213> ORGANISM: Artificial Sequence
<220> FEATURE:
<223> OTHER INFORMATION: Chemically synthesized - Primer PCR2-DN

<400> SEQUENCE: 10
cttctcctac cactaaaaa                                          19

<210> SEQ ID NO 11
<211> LENGTH: 19
<212> TYPE: DNA
<213> ORGANISM: Artificial Sequence
<220> FEATURE:

<223> OTHER INFORMATION: Chemically synthesized - Primer UP

<400> SEQUENCE: 11
aagcacctgt acccacacg                                                     19

<210> SEQ ID NO 12
<211> LENGTH: 18
<212> TYPE: DNA
<213> ORGANISM: Artificial Sequence
<220> FEATURE:
<223> OTHER INFORMATION: Chemically synthesized - Primer DN

<400> SEQUENCE: 12
ggctcaggga tcccacag                                                      18

<210> SEQ ID NO 13
<211> LENGTH: 21
<212> TYPE: DNA
<213> ORGANISM: Artificial Sequence
<220> FEATURE:
<223> OTHER INFORMATION: Primer UP

<400> SEQUENCE: 13
tcatccaggg cctggtcatc g                                                  21

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 14
tgtctgaggc cgacacggcc                                                    20

<210> SEQ ID NO 15
<211> LENGTH: 17
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (10)..(10)
<223> OTHER INFORMATION: "n" stands for C or T

<400> SEQUENCE: 15
ccccctcccn ggccccc                                                       17

<210> SEQ ID NO 16
<211> LENGTH: 17
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (10)..(10)
<223> OTHER INFORMATION: "n" stands for C or T

<400> SEQUENCE: 16
acccagggcn ccttgag                                                       17

<210> SEQ ID NO 17
<211> LENGTH: 20

```
<212> TYPE: DNA
<213> ORGANISM: Artificial Sequence
<220> FEATURE:
<223> OTHER INFORMATION: Chemically synthesized - Primer UP

<400> SEQUENCE: 17
gtgcattatc gggaggtatg                                                  20

<210> SEQ ID NO 18
<211> LENGTH: 25
<212> TYPE: DNA
<213> ORGANISM: Artificial Sequence
<220> FEATURE:
<223> OTHER INFORMATION: Chemically synthesized - Primer DN

<400> SEQUENCE: 18
accctgtatg atactgtaac tctgg                                            25

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: repeat_unit
<222> LOCATION: (10)..(11)
<223> OTHER INFORMATION: This unit is repeated any number of times in
      the sequence

<400> SEQUENCE: 19
atagggttag tagatcagtc                                                  20

<210> SEQ ID NO 20
<211> LENGTH: 22
<212> TYPE: DNA
<213> ORGANISM: Artificial Sequence
<220> FEATURE:
<223> OTHER INFORMATION: Chemically synthesized - Primer UP

<400> SEQUENCE: 20
ctttgaggtc catcatgttc ca                                               22

<210> SEQ ID NO 21
<211> LENGTH: 21
<212> TYPE: DNA
<213> ORGANISM: Artificial Sequence
<220> FEATURE:
<223> OTHER INFORMATION: Chemically synthesized - Primer DN

<400> SEQUENCE: 21
ggacgtacat cccatcgatg a                                                21

<210> SEQ ID NO 22
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 22
atggttgtcc tctgcgtggg c                                                21

<210> SEQ ID NO 23
<211> LENGTH: 21
<212> TYPE: DNA
```

<213> ORGANISM: Artificial Sequence
<220> FEATURE:
<223> OTHER INFORMATION: Chemically synthesized - Primer DN

<400> SEQUENCE: 23
tggcggtcga cgtgcagcat c                                             21

<210> SEQ ID NO 24
<211> LENGTH: 19
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for C or T

<400> SEQUENCE: 24
tgggtggggg ngcagcccc                                                19

<210> SEQ ID NO 25
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (8)..(8)
<223> OTHER INFORMATION: "n" stands for C or T
<220> FEATURE:
<221> NAME/KEY: misc_feature
<222> LOCATION: (15)..(15)
<223> OTHER INFORMATION: "n" stands for G or A

<400> SEQUENCE: 25 gctgggganca gaccntctgg g                                            21

<210> SEQ ID NO 26
<211> LENGTH: 22
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (13)..(13)
<223> OTHER INFORMATION: "n" stands for C or T

<400> SEQUENCE: 26
ctgtctgctc atncgggggc tg                                            22

<210> SEQ ID NO 27
<211> LENGTH: 22
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (13)..(13)
<223> OTHER INFORMATION: "n" stands for C or T

<400> SEQUENCE: 27
ggctgcggga gcntggggcc ac                                            22

```
<210> SEQ ID NO 28
<211> LENGTH: 22
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (13)..(13)
<223> OTHER INFORMATION: "n" stands for C or T

<400> SEQUENCE: 28
gccacccccg ccntgaccct ga                                              22

<210> SEQ ID NO 29
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 29
atccgcttcc tccagatcct g                                               21

<210> SEQ ID NO 30
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 30
gccgatgtac agcgtggtga                                                 20

<210> SEQ ID NO 31
<211> LENGTH: 18
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for G or T

<400> SEQUENCE: 31
tctgggccgg ngtccccg                                                   18

<210> SEQ ID NO 32
<211> LENGTH: 18
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for A or G

<400> SEQUENCE: 32
aaaagggtcc nggaagct                                                   18

<210> SEQ ID NO 33
<211> LENGTH: 21
```

```
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 33
ttgcaaacag cncccagaag g                                           21

<210> SEQ ID NO 34
<211> LENGTH: 21
<212> TYPE: DNA
<213> ORGANISM: Artificial Sequence
<220> FEATURE:
<223> OTHER INFORMATION: DChemically synthesized - NA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 34
agaaggcgca gnctccacgg g                                           21

<210> SEQ ID NO 35
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for C or T

<400> SEQUENCE: 35
agggcgctgg ntgcaggggt g                                           21

<210> SEQ ID NO 36
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for A or G

<400> SEQUENCE: 36
tttatgagtc ncaaaaacga g                                           21

<210> SEQ ID NO 37
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T
<220> FEATURE:
<221> NAME/KEY: misc_feature
```

```
<222> LOCATION: (13)..(13)
<223> OTHER INFORMATION: "n" stands for G or T

<400> SEQUENCE: 37
tgatgtccgc cnnggcagac t                                              21

<210> SEQ ID NO 38
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 38
gccccaagcc caagaagtct g                                              21

<210> SEQ ID NO 39
<211> LENGTH: 21
<212> TYPE: DNA
<213> ORGANISM: Artificial Sequence
<220> FEATURE:
<223> OTHER INFORMATION: Chemically synthesized - Primer DN

<400> SEQUENCE: 39
ccagaattgt cacagccatc c                                              21

<210> SEQ ID NO 40
<211> LENGTH: 20
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for A or G

<400> SEQUENCE: 40
tccggggcat ntaggactgg                                                20

<210> SEQ ID NO 41
<211> LENGTH: 23
<212> TYPE: DNA
<213> ORGANISM: Artificial Sequence
<220> FEATURE:
<223> OTHER INFORMATION: Chemically synthesized - Primer UP

<400> SEQUENCE: 41
ggagtacctg ctgtggctta gtg                                            23

<210> SEQ ID NO 42
<211> LENGTH: 25
<212> TYPE: DNA
<213> ORGANISM: Artificial Sequence
<220> FEATURE:
<223> OTHER INFORMATION: Chemically synthesized - Primer DN

<400> SEQUENCE: 42
cgtcctatat ccatcaggaa tattg                                          25

<210> SEQ ID NO 43
<211> LENGTH: 18
<212> TYPE: DNA
<213> ORGANISM: Artificial Sequence
<220> FEATURE:
<223> OTHER INFORMATION: Chemically synthesized - DNA Sequence
```

```
      Polymorphisms (DSP)
<220> FEATURE:
<221> NAME/KEY: misc_feature
<222> LOCATION: (9)..(9)
<223> OTHER INFORMATION: "n" stands for C or T

<400> SEQUENCE: 43
agtagtatnc atgagcac                                                 18

<210> SEQ ID NO 44
<211> LENGTH: 23
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (11)..(11)
<223> OTHER INFORMATION: "n" stands for G or A

<400> SEQUENCE: 44
cccaggcctc natcagctgg ttg                                           23

<210> SEQ ID NO 45
<211> LENGTH: 22
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (10)..(10)
<223> OTHER INFORMATION: "n" stands for C or A

<400> SEQUENCE: 45
tatatgccan acatgtggcc ct                                            22

<210> SEQ ID NO 46
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 46
ggggccatcc aggagtcaca g                                             21

<210> SEQ ID NO 47
<211> LENGTH: 21
<212> TYPE: DNA
<213> ORGANISM: Artificial Sequence
<220> FEATURE:
<223> OTHER INFORMATION: Chemically synthesized - Primer DN

<400> SEQUENCE: 47
caaagaggat cacgaggcag g                                             21

<210> SEQ ID NO 48
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 48
tgcgtagcca tggcgatggg g                                             21
```

<210> SEQ ID NO 49
<211> LENGTH: 25
<212> TYPE: DNA
<213> ORGANISM: Artificial Sequence
<220> FEATURE:
<223> OTHER INFORMATION: Chemically synthesized - Primer DN

<400> SEQUENCE: 49
agtgtggaac cctgggggggg gaagg                                    25

<210> SEQ ID NO 50
<211> LENGTH: 19
<212> TYPE: DNA
<213> ORGANISM: Artificial Sequence
<220> FEATURE:
<223> OTHER INFORMATION: Chemically synthesized - Primer UP

<400> SEQUENCE: 50
agagggtaca gaagccctg                                            19

<210> SEQ ID NO 51
<211> LENGTH: 23
<212> TYPE: DNA
<213> ORGANISM: Artificial Sequence
<220> FEATURE:
<223> OTHER INFORMATION: Chemically synthesized - Primer DN

<400> SEQUENCE: 51
tttggtgtgg tgtctgctga ccc                                       23

<210> SEQ ID NO 52
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 52
aggctttcta tctgcaggag g                                         21

<210> SEQ ID NO 53
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 53
accgtgtggc catctgggtg                                           20

<210> SEQ ID NO 54
<211> LENGTH: 20
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: repeat_unit
<222> LOCATION: (10)..(11)
<223> OTHER INFORMATION: This unit is repeated any number of times in
      the sequence

<400> SEQUENCE: 54
tctctgtatc acgcacgcac                                           20

<210> SEQ ID NO 55
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 55
gcgttgcagt ggctctggcg                                               20

<210> SEQ ID NO 56
<211> LENGTH: 21
<212> TYPE: DNA
<213> ORGANISM: Artificial Sequence
<220> FEATURE:
<223> OTHER INFORMATION: Chemically synthesized - Primer DN

<400> SEQUENCE: 56
gacacggccg catgaatgtg c                                             21

<210> SEQ ID NO 57
<211> LENGTH: 20
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: repeat_unit
<222> LOCATION: (10)..(11)
<223> OTHER INFORMATION: This unit is repeated any number of times in
      the sequence

<400> SEQUENCE: 57
accccaacat aattatggta                                               20

<210> SEQ ID NO 58
<211> LENGTH: 22
<212> TYPE: DNA
<213> ORGANISM: Artificial Sequence
<220> FEATURE:
<223> OTHER INFORMATION: Chemically synthesized - Primer UP

<400> SEQUENCE: 58
gcccgtctac ttcgtgtctg ag                                            22

<210> SEQ ID NO 59
<211> LENGTH: 23
<212> TYPE: DNA
<213> ORGANISM: Artificial Sequence
<220> FEATURE:
<223> OTHER INFORMATION: Chemically synthesized - Primer DN

<400> SEQUENCE: 59
atctctgcct tcatcgcacc ccc                                           23

<210> SEQ ID NO 60
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for A or T

```
<400> SEQUENCE: 60
aggatccagc cngcagcccc g                                              21

<210> SEQ ID NO 61
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)

<400> SEQUENCE: 61
tcacaacccc cctcccacag c                                              21

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized - DNA Sequence
      Polymorphisms (DSP)

<400> SEQUENCE: 62
tcacaacccc ctcccacagc                                                20

<210> SEQ ID NO 63
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for A or G

<400> SEQUENCE: 63
ctgcggaggg gngacctgca g                                              21

<210> SEQ ID NO 64
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 64
gctgcggacc ccaccgtcac                                                20

<210> SEQ ID NO 65
<211> LENGTH: 23
<212> TYPE: DNA
<213> ORGANISM: Artificial Sequence
<220> FEATURE:
<223> OTHER INFORMATION: Chemically synthesized - Primer DN

<400> SEQUENCE: 65
agacttcacc cctaaaagcc tgg                                            23

<210> SEQ ID NO 66
<211> LENGTH: 25
<212> TYPE: DNA
<213> ORGANISM: Artificial Sequence
<220> FEATURE:
<223> OTHER INFORMATION: Chemically synthesized - DNA Sequence
      Polymorphisms (DSP)
```

```
<400> SEQUENCE: 66
gccaggtcaa ggccaggtcg aggcc                                          25

<210> SEQ ID NO 67
<211> LENGTH: 14
<212> TYPE: DNA
<213> ORGANISM: Artificial Sequence
<220> FEATURE:
<223> OTHER INFORMATION: Chemically synthesized - DNA Sequence
      Polymorphisms (DSP)

<400> SEQUENCE: 67
gccaggtcga ggcc                                                      14

<210> SEQ ID NO 68
<211> LENGTH: 19
<212> TYPE: DNA
<213> ORGANISM: Artificial Sequence
<220> FEATURE:
<223> OTHER INFORMATION: Chemically synthesized - Primer UP

<400> SEQUENCE: 68
agcaggctgc tgtgctggg                                                 19

<210> SEQ ID NO 69
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 69
agcccagacc cagctgacgg                                                20

<210> SEQ ID NO 70
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for G or A

<400> SEQUENCE: 70
ggcgcttatg gngccgggag c                                              21

<210> SEQ ID NO 71
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (10)..(10)
<223> OTHER INFORMATION: "n" stands for G or T

<400> SEQUENCE: 71
caagcccggn cggtttggcc t                                              21

<210> SEQ ID NO 72
<211> LENGTH: 21
```

```
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for A or G

<400> SEQUENCE: 72
ctaatgacct cnaggccccc a                                              21

<210> SEQ ID NO 73
<211> LENGTH: 22
<212> TYPE: DNA
<213> ORGANISM: Artificial Sequence
<220> FEATURE:
<223> OTHER INFORMATION: Chemically synthesized - Primer UP

<400> SEQUENCE: 73
tgatgaccca cggagatgat cc                                             22

<210> SEQ ID NO 74
<211> LENGTH: 28
<212> TYPE: DNA
<213> ORGANISM: Artificial Sequence
<220> FEATURE:
<223> OTHER INFORMATION: Chemically synthesized - Primer DN

<400> SEQUENCE: 74
gcagtagttc tccagctggt agagggaa                                       28

<210> SEQ ID NO 75
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 75
gggaccagct gngttcccag g                                              21

<210> SEQ ID NO 76
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or G

<400> SEQUENCE: 76
gccctgctgg cnctctgggc g                                              21

<210> SEQ ID NO 77
<211> LENGTH: 21
<212> TYPE: DNA
<213> ORGANISM: Artificial Sequence
<220> FEATURE:
<223> OTHER INFORMATION: Chemically synthesized - DNA Sequence
```

```
        Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 77
ctcccacgcc cnggtcccgc t                                            21

<210> SEQ ID NO 78
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 78
gctctcgcca catcggctgc                                              20

<210> SEQ ID NO 79
<211> LENGTH: 22
<212> TYPE: DNA
<213> ORGANISM: Artificial Sequence
<220> FEATURE:
<223> OTHER INFORMATION: Chemically synthesized - Primer DN

<400> SEQUENCE: 79
ggcgcccagc tctaggcccg gc                                           22

<210> SEQ ID NO 80
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for G or A

<400> SEQUENCE: 80
gggctggctg cngtctggga g                                            21

<210> SEQ ID NO 81
<211> LENGTH: 25
<212> TYPE: DNA
<213> ORGANISM: Artificial Sequence
<220> FEATURE:
<223> OTHER INFORMATION: Chemically synthesized - Primer UP

<400> SEQUENCE: 81
cccctgaact tgaggacgag cagcc                                        25

<210> SEQ ID NO 82
<211> LENGTH: 23
<212> TYPE: DNA
<213> ORGANISM: Artificial Sequence
<220> FEATURE:
<223> OTHER INFORMATION: Chemically synthesized - Primer DN

<400> SEQUENCE: 82
cgctgtgggc tgggtgggct gcc                                          23

<210> SEQ ID NO 83
<211> LENGTH: 21
<212> TYPE: DNA
```

```
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for A or G

<400> SEQUENCE: 83
gctgcccccc ancctgagct g                                              21

<210> SEQ ID NO 84
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 84
cttgcctcca actccctccc                                                20

<210> SEQ ID NO 85
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 85
agtgaacgtg aaacgggggg                                                20

<210> SEQ ID NO 86
<211> LENGTH: 24
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: repeat_unit
<222> LOCATION: (12)..(13)
<223> OTHER INFORMATION: This unit is repeated any number of times in
      the sequence

<400> SEQUENCE: 86
ctctcgctgt cctcgccctc tctt                                           24

<210> SEQ ID NO 87
<211> LENGTH: 21
<212> TYPE: DNA
<213> ORGANISM: Artificial Sequence
<220> FEATURE:
<223> OTHER INFORMATION: Chemically synthesized - Primer UP

<400> SEQUENCE: 87
tgcgccaccc ccgccaagtc c                                              21

<210> SEQ ID NO 88
<211> LENGTH: 23
<212> TYPE: DNA
<213> ORGANISM: Artificial Sequence
<220> FEATURE:
<223> OTHER INFORMATION: Chemically synthesized - Primer DN

<400> SEQUENCE: 88
gcttccaggt gtcatagcgg aag                                            23
```

```
<210> SEQ ID NO 89
<211> LENGTH: 22
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: repeat_unit
<222> LOCATION: (12)..(13)
<223> OTHER INFORMATION: This unit is repeated any number of times in
      the sequence

<400> SEQUENCE: 89
agccggctcc tgcggcttca ag                                              22

<210> SEQ ID NO 90
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 90
agaggttgtt gntctgggac a                                               21

<210> SEQ ID NO 91
<211> LENGTH: 19
<212> TYPE: DNA
<213> ORGANISM: Artificial Sequence
<220> FEATURE:
<223> OTHER INFORMATION: Chemically synthesized - UP-primer SWC9

<400> SEQUENCE: 91
aagcacctgt acccacacg                                                  19

<210> SEQ ID NO 92
<211> LENGTH: 18
<212> TYPE: DNA
<213> ORGANISM: Artificial Sequence
<220> FEATURE:
<223> OTHER INFORMATION: Chemically synthesized - DN-primer SWC9

<400> SEQUENCE: 92
ggctcaggga tcccacag                                                   18

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 93
caagccaggt cctgtcgagg                                                 20

<210> SEQ ID NO 94
<211> LENGTH: 18
<212> TYPE: DNA
<213> ORGANISM: Artificial Sequence
<220> FEATURE:
<223> OTHER INFORMATION: Chemically synthesized - Primer DN
```

```
<400> SEQUENCE: 94
ggaccctggg ggctgtgg                                                    18

<210> SEQ ID NO 95
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for A or G

<400> SEQUENCE: 95
cggcctgtgg cnggaagct g                                                 21

<210> SEQ ID NO 96
<211> LENGTH: 19
<212> TYPE: DNA
<213> ORGANISM: Artificial Sequence
<220> FEATURE:
<223> OTHER INFORMATION: Chemically synthesized - Primer UP

<400> SEQUENCE: 96
acggtcccgg gtcagcagg                                                   19

<210> SEQ ID NO 97
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 97
cagagcaagt gggcacccag                                                  20

<210> SEQ ID NO 98
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 98
cgcgggtttg gncagcggca g                                                21

<210> SEQ ID NO 99
<211> LENGTH: 21
<212> TYPE: DNA
<213> ORGANISM: Artificial Sequence
<220> FEATURE:
<223> OTHER INFORMATION: Chemically synthesized - DNA Sequence
    Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 99
cacagaggac anggccgctt c                                                21
```

<210> SEQ ID NO 100
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 100
tcctgggggc cngcggctcg t                                              21

<210> SEQ ID NO 101
<211> LENGTH: 22
<212> TYPE: DNA
<213> ORGANISM: Artificial Sequence
<220> FEATURE:
<223> OTHER INFORMATION: Chemically synthesized - Primer UP

<400> SEQUENCE: 101
gagcacagcc aaagaacggc cg                                             22

<210> SEQ ID NO 102
<211> LENGTH: 22
<212> TYPE: DNA
<213> ORGANISM: Artificial Sequence
<220> FEATURE:
<223> OTHER INFORMATION: Chemically synthesized - Primer DN

<400> SEQUENCE: 102
cttcacccac ggacatggcc gc                                             22

<210> SEQ ID NO 103
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 103
cacccaggct gngccctgcg t                                              21

<210> SEQ ID NO 104
<211> LENGTH: 18
<212> TYPE: DNA
<213> ORGANISM: Artificial Sequence
<220> FEATURE:
<223> OTHER INFORMATION: Chemically synthesized - Primer UP

<400> SEQUENCE: 104
cgggggcact gggggtcc                                                  18

<210> SEQ ID NO 105
<211> LENGTH: 20
<212> TYPE: DNA
<213> ORGANISM: Artificial Sequence
<220> FEATURE:
<223> OTHER INFORMATION: Chemically synthesized - Primer DN

<400> SEQUENCE: 105

```
ccgagaccct cctcaagtcc                                              20

<210> SEQ ID NO 106
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for A or G

<400> SEQUENCE: 106
gttcgccctc cnctctcagc a                                            21

<210> SEQ ID NO 107
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 107
tgagctgctg agcccacagg                                              20

<210> SEQ ID NO 108
<211> LENGTH: 21
<212> TYPE: DNA
<213> ORGANISM: Artificial Sequence
<220> FEATURE:
<223> OTHER INFORMATION: Chemically synthesized - Primer DN

<400> SEQUENCE: 108
caagggaaag gtgtgccgac c                                            21

<210> SEQ ID NO 109
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 109
ggccgggcgc tncgccttcc c                                            21

<210> SEQ ID NO 110
<211> LENGTH: 20
<212> TYPE: DNA
<213> ORGANISM: Artificial Sequence
<220> FEATURE:
<223> OTHER INFORMATION: Chemically synthesized - Primer UP

<400> SEQUENCE: 110
aggcagaggg cagagagggg                                              20

<210> SEQ ID NO 111
<211> LENGTH: 19
<212> TYPE: DNA
<213> ORGANISM: Artificial Sequence
<220> FEATURE:
```

-continued

<223> OTHER INFORMATION: Chemically synthesized - Primer DN

<400> SEQUENCE: 111
ctccagcccc acactctgc                                                    19

<210> SEQ ID NO 112
<211> LENGTH: 21
<212> TYPE: DNA
<213> ORGANISM: Artificial Sequence
<220> FEATURE:
<223> OTHER INFORMATION: Chemically synthesized - DNA Sequence
      Polymorphisms (DSP)
<220> FEATURE:
<221> NAME/KEY: misc_feature
<222> LOCATION: (12)..(12)
<223> OTHER INFORMATION: "n" stands for C or T

<400> SEQUENCE: 112
gcgtccagcg cngaatcagg c                                                 21

<210> SEQ ID NO 113
<211> LENGTH: 14
<212> TYPE: DNA
<213> ORGANISM: Artificial Sequence
<220> FEATURE:
<223> OTHER INFORMATION: Chemically synthesized - MH1

<400> SEQUENCE: 113
tcgcaaggcc aggt                                                         14

<210> SEQ ID NO 114
<211> LENGTH: 14
<212> TYPE: DNA
<213> ORGANISM: Artificial Sequence
<220> FEATURE:
<223> OTHER INFORMATION: Chemically synthesized - MH3

<400> SEQUENCE: 114
acgcaaggcc aggt                                                         14

<210> SEQ ID NO 115
<211> LENGTH: 94
<212> TYPE: DNA
<213> ORGANISM: Sus scrofa

<400> SEQUENCE: 115
agccagggac gagcctgccc gcggcggcag ccgggccgcg gcttcgccta ggctcgcagc      60
gcgggagcgc gtggggcgcg gcggcggcgg ggag                                   94

<210> SEQ ID NO 116
<211> LENGTH: 94
<212> TYPE: DNA
<213> ORGANISM: Sus scrofa

<400> SEQUENCE: 116
agccagggac gagcctgccc gcggcggcag ccgggccgcg gcttcgccta ggctcacagc      60
gcgggagcgc gtggggcgcg gcggcggcgg ggag                                   94

<210> SEQ ID NO 117
<211> LENGTH: 94
<212> TYPE: DNA
<213> ORGANISM: Homo sapiens

<400> SEQUENCE: 117

-continued

```
agccggggac tagcctgctc ccggtggcgg ctcggccgcg gcttcgccta ggctcgcagc    60
gcggaggcga gtggggcgca gtggcgaggg ggag                                94

<210> SEQ ID NO 118
<211> LENGTH: 94
<212> TYPE: DNA
<213> ORGANISM: Mus musculus

<400> SEQUENCE: 118
agctagggac gagtctgccc ccggcggctg cctggccccg acttcgccta ggctcgcggc    60
gtctgagcgc gtggggcgca ggggcggcgg ggag                                94
```

What is claimed is:

1. A method for selecting a pig having a desired genotypic property, said method comprising:
   testing a population of pigs for the presence of a nucleic acid sequence;
   wherein said nucleic acid sequence comprises a nucleotide substitution in 5'-GATCCTTCGCCTAGGCTCNCAGCGCGGGAGCGA-3' (SEQ ID NO: 1)
   wherein said nucleic acid sequence has increased mobility relative to 5'-GATCCTTCGCCTAGGCTCNCAGCGCGGGAGCGA-3' (SEQ ID NO:1) during gel electrophoresis after exposure of said nucleic acid sequence and 5'-GATCCTTCGCCTAGGCTCNCAGCGCGGGAGCGA-3' (SEQ ID NO:1) to extracts from C2C12 myoblast cells; and
   selecting, from the population of pigs tested, a pig comprising said nucleic acid sequence, a parent of said pig, or a progeny of said pig.

2. The method according to claim 1, wherein said nucleotide substitution comprises a substitution of A for G at position 19 of 5'-GATCCTTCGCCTAGGCTCNCAGCGCGGGAGCGA-3' (SEQ ID NO:1).

3. A method for selecting a pig having desired genotypic or potential phenotypic properties, the method comprising:
   testing said pig, a parent of said pig or its progeny, for the presence of a nucleic acid modification located in intron 3 of an IGF2 gene, wherein the nucleic acid modification comprises a nucleotide substitution comprising a G to A transition at IGF2-intron3-nt3072, and
   selecting, from a population of pigs tested, a pig comprising said nucleic acid sequence, a parent of said pig, or a progeny of said pig;
   wherein said desired genotypic or potential phenotypic properties comprise muscle mass, teat number, fat deposition, lean meat, lean back fat, sow prolificacy and/or sow longevity.

4. The method according to claim 3, wherein said sow prolificacy includes such phenotypic expressions as teat number, number of piglets born alive, litter size, number of total born and/or number of weaned piglets.

5. The method according to claim 3, wherein said sow longevity includes such phenotypic expressions as parity and/or average number of cycles per sow.

6. A method of enhancing a breeding program, the method comprising:
   selecting a pig according to the method of claim 5; and
   incorporating the selected pig in a pig breeding program so as to enhance performance of breeding pigs or pigs destined for slaughter and to facilitate introgression of the nucleic acid modification to additional breeds.

7. A method for selecting a pig having a desired genotypic property, said method comprising:
   testing a population of pigs for the presence of a nucleic acid sequence;
   wherein said nucleic acid sequence is located in a CpG island within intron 3 of an IGF2 gene and has at least 50% homology with the sequence 5'-GATCCTTCGCCTAGGCTCNCAGCGCGGGAGCGA-3' (SEQ ID NO: 1);
   wherein said nucleic acid sequence has increased mobility relative to 5'-GATCCTTCGCCTAGGCTCNCAGCGCGGGAGCGA-3' (SEQ ID NO:1) during gel electrophoresis after exposure of said nucleic acid sequence and 5'-GATCCTTCGCCTAGGCTCNCAGCGCGGGAGCGA-3' (SEQ ID NO:1) to extracts from C2C12 myoblast cells; and
   selecting, from the population of pigs tested, a pig comprising said nucleic acid sequence, a parent of said pig, or a progeny of said pig.

8. The method according to claim 7, wherein said nucleic acid sequence comprises a substitution of A for G at position 19 of 5'-GATCCTTCGCCTAGGCTCNCAGCGCGGGAGCGA-3' (SEQ ID NO: 1).

* * * * *